(12) United States Patent
Takata et al.

(10) Patent No.: US 7,678,884 B2
(45) Date of Patent: Mar. 16, 2010

(54) BIOLOGICALLY ACTIVE PEPTIDE AND AGENT CONTAINING THE SAME

(75) Inventors: Takashi Takata, Hiroshima (JP); Shoji Kitagawa, Kure (JP); Yuji Kaneda, Tama (JP)

(73) Assignee: Seikagaku Corporation, Tokyo (JP)

( * ) Notice: Subject to any disclaimer, the term of this patent is extended or adjusted under 35 U.S.C. 154(b) by 32 days.

(21) Appl. No.: 12/052,578

(22) Filed: Mar. 20, 2008

(65) Prior Publication Data
US 2009/0137482 A1 May 28, 2009

Related U.S. Application Data

(62) Division of application No. 10/546,223, filed as application No. PCT/JP2004/002009 on Feb. 20, 2004, now Pat. No. 7,365,153.

(30) Foreign Application Priority Data

| Feb. 21, 2003 | (JP) | ............................. 2003-045166 |
| May 21, 2003 | (JP) | ............................. 2003-142845 |

(51) Int. Cl.
*C07K 7/00* (2006.01)
(52) U.S. Cl. ........................................ 530/326; 514/14
(58) Field of Classification Search ................. 530/326; 514/14
See application file for complete search history.

(56) References Cited

U.S. PATENT DOCUMENTS

2001/0039335 A1  11/2001  Jacobs et al.
2002/0106333 A1   8/2002  Cerny et al.

FOREIGN PATENT DOCUMENTS

| EP | 1 165 102 B1 | 1/2004 |
| WO | WO 97/02730 | 1/1997 |
| WO | WO 99/35253 | 7/1999 |
| WO | WO 99/43344 | 9/1999 |

OTHER PUBLICATIONS

Begue-Kim, et al. "Dentin Sialoprotein, Dentin Phosphoprotein, Enamelysin and Ameloblastin: Tooth-Specific Molecules that are Distinctively Expressed During Murine Dental Differentiation," *European Journal of Oral Sciences*, vol. 106, No. 5, pp. 963-970, Oct. 1998.

Cerny, et al. "A Novel Gene Expressed in Rat Ameloblasts Codes for Proteins with Cell Binding Domains," *Journal of Bone and Mineral Research*, vol. 11, No. 7, pp. 883-891, 1996.

Fong, et al. "Sequential Expression of an Amelin Gene in Mesenchymal and Epithelial Cells During Odontogenesis in Rats," *European Journal of Oral Sciences*, vol. 106, Supplement 1, pp. 324-330, 1998.

Hu, et al. "Sheathlin: Cloning, cDNA/Polypeptide Sequences, and Immunolocalization of Porcine Enamel Sheath Proteins," *Journal of Dental Research*, vol. 76, No. 2, pp. 648-657, Feb. 1997.

Krebsbach, et al. "Full-Length Sequence, Localization, and Chromosomal Mapping of Ameloblastin," *The Journal of Biological Chemistry*, vol. 271, No. 8, pp. 4431-4435, Feb. 23, 1996.

MacDougall, et al. "Cloning, Characterization and Immunolocalization of Human Ameloblastin," *European Journal of Oral Sciences*, vol. 108, No. 4, pp. 303-310, Aug. 2000.

Takata, et al. "Immunohistochemical Demonstration of an Enamel Sheath Protein, Sheathlin, in Odontogenic Tumors," *Virchows Archiv, Official Journal of the European Society of Pathology*, vol. 436, No. 4, pp. 324-329, Apr. 2000.

Toyosawa, et al. "Cloning and Characterization of the Human Ameloblastin Gene," *Gene*, vol. 256, pp. 1-11, 2000.

Uchida, et al. "Synthesis, Secretion, Degradation, and Fate of Ameloblastin During the Matrix Formation Stage of the Rat Incisor as Shown by Immunocytochemistry and Immunochemistry Using Region-Specific Antibodies," *The Journal of Histochemistry & Cytochemistry*, vol. 45, No. 10, pp. 1329-1340, 1997.

Uchida, et al. "Sheath Proteins: Synthesis, Secretion, Degradation and Fate in Forming Enamel," *European Journal of Oral Sciences*, vol. 106, Supp. 1, pp. 308-314, Jan. 1998.

Uchida, et al. "Immunochemical and Immunocytochemical Study of a 15kDa Non-Amelogenin and Related Proteins in the Porcine Immature Enamel: Proposal of a New Group of Enamel Proteins 'Sheath Proteins,'" *Biomedical Research 1995 Japan*, vol. 16, No. 3, pp. 131-140, 1995.

Abstract of Mao, Yumin (CN 1302883A) Jul. 2001.
European Search Report for PCT/JP04/02009, Jun. 2007.

*Primary Examiner*—David Lukton
(74) *Attorney, Agent, or Firm*—Knobbe, Martens, Olson & Bear, LLP

(57) ABSTRACT

A peptide having any one of the amino acid sequences of SEQ ID NO: 1 or 13, preferably a peptide having any one of the amino acid sequences of SEQ ID NOS: 2 to 9 or a peptide having any one of the amino acid sequences of SEQ ID NOS: 10 and 15 to 17, is used as an active ingredient of an agent for promoting growth or differentiation of cells such as osteoblasts, chondroblasts, cementoblasts, bone marrow-derived mesenchymal stem cells and periodontal ligament-derived cells.

11 Claims, 13 Drawing Sheets

ID NO: 1# BIOLOGICALLY ACTIVE PEPTIDE AND AGENT CONTAINING THE SAME

RELATED APPLICATIONS

This application is a divisional of U.S. application Ser. No. 10/546,223, filed Aug. 18, 2005, now U.S. Pat. No. 7,365,153, issued Apr. 29, 2008 which is the U.S. National Phase under 35 U.S.C. § 371 of International Application PCT/JP2004/002009, filed Feb. 20, 2004, which was published in a language other than English which claims priority of JP 2003-045166, filed Feb. 21, 2003 and JP 2003-142845, filed May 21, 2003.

TECHNICAL FIELD

The present invention relates to a novel biologically active peptide. The present invention also relates to an agent containing this biologically active peptide as an active ingredient. The peptide and the agent of the present invention are useful in the field of pharmaceutical and so forth.

BACKGROUND ART

Sheathlin is a protein that exists in the enamel matrix and is also referred to as ameloblastin or amelin. Amino acid sequences of sheathlins in swine, human, bovine, mouse and rat are already known (ameloblastin derived from the rat incisor: Krebsbach P H, Lee S K, Matsuki Y, Kozack C A, Yamada K and Yamada Y, Full-length sequence, localization, and chromosomal mapping of ameloblastin. A novel tooth specific gene., J. Biol. Chem., 271: 4431-4435, 1996; amelin derived from the rat molar: Cerny R, Slaby I, Hammarstrm L and Wuitz T: A novel gene expressed in rat ameloblasts codes for proteins with cell binding domains., J. Bone Miner. Res., 11: 883-891, 1996; sheathlin derived from swine: Hu C C, Fukae M, Uchida T, Qian Q, Zhang C H, Ryu O H, Tanabe T, Yamakoshi Y, Murakami C, Dohi N, Shimizu M and Simmer J P: Sheathlin: Cloning, cDNA/polypeptide sequences, and immunolocalozation of porcine enamel sheath proteins., J. Dent. Res., 76: 648-657, 1997; sheathlins derived from human, bovine and mouse: Toyosawa S, Fujiwara T, Ooshima T, Shintani S, Sato A, Ogawa Y, Sobue S and Ijuhin N: Cloning and characterization of the human ameloblastin gene., Gene, 256: 1-11, 2000).

Further, an antibody that recognizes the sequence of the 27th to 47th amino acid residues of sheathlin (derived from rat, corresponding to SEQ ID NO: 6) has been disclosed (The Journal of Histochemistry & Cytochemistry, 45(10), 1329-1340 (1997)). However, this publication only discloses that a certain particular antibody recognizes such an amino acid sequence and does not disclose nor suggest production of a peptide having such an amino acid sequence or use of the peptide for pharmaceutical purposes and so forth.

Further, various pharmaceutical uses of a tetrapeptide derived from amelin and various pharmaceutical uses of amelin (therapeutic and prophylactic treatments of periodontal diseases, repair of tooth lesions, bonding of bone elements, promotion or induction of mineralization of hard tissues, effective uptake of an implant into the bone, improvement of biocompatibility of implant instruments etc.) have been reported (International Patent Application Unexamined Publication in Japanese (Kohyo) No. 11-510377). However, the peptide of the present invention described later, pharmaceutical use thereof and so forth have not been disclosed nor suggested.

DISCLOSURE OF THE INVENTION

The various pharmaceutical uses are known for sheathlin as described above. If an amino acid sequence in the biologically active sheathlin is identified and a peptide having this amino acid sequence can be obtained, a pharmaceutical material that can more effectively exhibit the biological activity of sheathlin can be provided at a lower cost.

The present invention was accomplished from the aforementioned point of view, and an object thereof is to provide a peptide derived from sheathlin and having a biological activity and a pharmaceutical containing the peptide as an active ingredient.

The inventors of the present invention assiduously studied in order to achieve the aforementioned object. As a result, they identified an amino acid sequence in sheathlin having a biological activity, produced a peptide having this amino acid sequence, found that the peptide exhibited various biological activities, and thus accomplished the present invention.

That is, the present invention provides a peptide having the following amino acid sequence (SEQ ID NO: 1) (hereinafter, referred to as the "peptide-N of the present invention"):

X01 Pro X02 X03 X04 X05 X06 X07 X08 X09 X10 X11 X12 X13 X14 X15 X16 X17 X18 X19 X20 wherein X01 represents Val or Gln, X02 represents Ala, Phe or Gly, X03 represents Phe or Leu, X04 represents Pro or Lys, X05 represents Arg, Gln or Pro, X06 represents Gln, Arg or Phe, X07 represents Pro, Ser or Leu, X08 indicates absence of amino acid residue or represents Gly or Gln, X09 indicates absence of amino acid residue or represents Ala, Gly or Pro, X10 indicates absence of amino acid residue or represents Gln or Thr, X11 indicates absence of amino acid residue or represents Gly or Ala, X12 indicates absence of amino acid residue or represents Met or Ala, X13 represents Gly, Ala or Thr, X14 represents Thr, Ile, Pro or Gly, X15 represents Pro or Val, X16 represents Gly or Gln, X17 represents Val, Met or Gly, X18 represents Ala or Thr, X19 represents Ser or Pro, and X20 represents Leu or Gln.

The peptide-N of the present invention preferably has the following amino acid sequence (SEQ ID NO: 2):

Val Pro X21 Phe Pro X22 Gln X23 Gly X24 Pro Gly X25 Ala Ser Leu wherein X21 represents Ala or Phe, X22 represents Arg or Gln, X23 represents Pro or Ser, X24 represents Thr or Ile, and X25 represents Val, Met or Gly.

The peptide-N of the present invention preferably has any of the following amino acid sequences (A) to (G):

(A) Val Pro Ala Phe Pro Arg Gln Pro Gly Thr Pro Gly Val Ala  (SEQ ID NO: 3)
    Ser Leu (B) Val Pro Phe Phe Pro Gln Gln Ser Gly Thr Pro Gly Met Ala  (SEQ ID NO: 4)
    Ser Leu

```
(C) Val Pro Ala Phe Pro Gln Gln Pro Gly Ile Pro Gly Met Ala  (SEQ ID NO: 5)
    Ser Leu (D) Val Pro Ala Phe Pro Gln Gln Pro Gly Ala Gln Gly Met Ala  (SEQ ID NO: 6)
    Pro Pro Gly Met Ala Ser Leu (E) Val Pro Ala Phe Pro Gln Arg Pro Gly Gly Gln Gly Met Ala  (SEQ ID NO: 7)
    Pro Pro Gly Met Ala Ser Leu (F) Gln Pro Gly Leu Lys Pro Phe Leu Gln Pro Thr Ala Ala Thr  (SEQ ID NO: 8)
    Gly Val Gln Val Thr Pro Gln (G) Val Pro Phe Phe Pro Gln Gln Ser Gly Thr Pro Gly Gly Ala  (SEQ ID NO: 9)
    Ser Leu
```

Among these, a peptide having the above amino acid sequence (A), (B) or (G) is preferred.

The present invention also provides a peptide having the following amino acid sequence (SEQ ID NO: 13) (hereinafter, referred to as the "peptide-C of the present invention"):
Asn Lys X26 X27 X28 Pro X28 X29 X30 X31 X32 Ala Trp X31 Phe
wherein X26 represents Ala or Val, X27 represents Gln or His, X28 represents Gln or Glu, X29 represents Ile, Met or Val, X30 indicates absence of amino acid residue or represents Lys or Met, X31 represents Arg or His, and X32 represents Asp or Asn.

The peptide-C of the present invention preferably has the following amino acid sequence (SEQ ID NO: 14):
Asn Lys Ala Gln X33 Pro X33 X34 X35 X36 Asp Ala Trp X36 Phe
wherein X33 represents Gln or Glu, X34 represents Ile or Met, X35 represents Lys or Met, and X36 represents Arg or His.

The peptide-C of the present invention preferably has any of the following amino acid sequences (H) to (K):

```
(H) Asn Lys Ala Gln Gln Pro Gln Ile Lys Arg Asp Ala Trp Arg  (SEQ ID NO: 10)
    Phe (I) Asn Lys Ala Gln Glu Pro Glu Met Met His Asp Ala Trp His  (SEQ ID NO: 15)
    Phe (J) Asn Lys Ala Gln Gln Pro Gln Ile Lys His Asp Ala Trp His  (SEQ ID NO: 16)
    Phe (K) Asn Lys Val His Gln Pro Gln Val His Asn Ala Trp Arg Phe  (SEQ ID NO: 17)
```

Among these, a peptide having the above amino acid sequence (H) or (I) is preferred.

Hereinafter, the peptide-N of the present invention and the peptide-C of the present invention are collectively referred to as the "peptide of the present invention."

Further, the present invention also provides an agent containing the peptide of the present invention as an active ingredient (hereinafter, referred to as the "agent of the present invention"). The agent of the present invention is preferably a pharmaceutical.

Further, the agent of the present invention is also preferably an agent for promoting cell growth or cell differentiation. The "cell" of which growth or differentiation is to be promoted is preferably an osteoblast, chondroblast, cementoblast, bone marrow-derived mesenchymal stem cell or periodontal ligament-derived cell.

Further, the agent of the present invention is also preferably an agent for promoting bone or cartilage formation or regeneration or an agent for promoting periodontal tissue formation or regeneration.

Further, the present invention provides a composition containing at least the peptide of the present invention and hyaluronic acid or a pharmaceutically acceptable salt thereof (hereinafter, referred to as the "composition of the present invention").

BEST MODE FOR CARRYING OUT THE INVENTION

Figure 1:
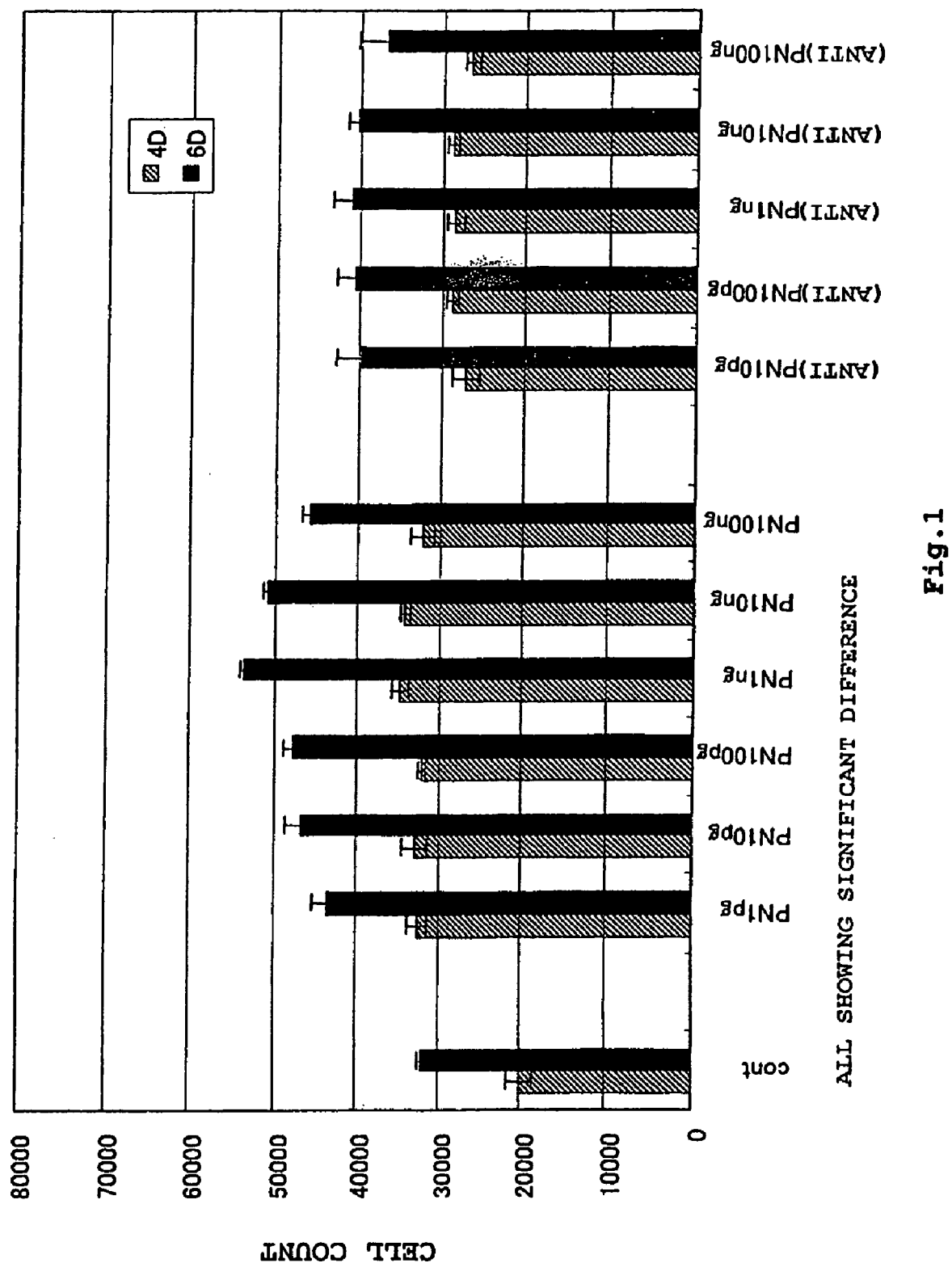
FIG. 1 shows the cell growth promoting effects of the peptide-N of the present invention (derived from swine) on the PDL cells (derived from human).

Hereafter, the present invention will be explained in detail.

<1> Peptide of the Present Invention (1) Peptide-N of the Present Invention

The peptide-N of the present invention is a peptide having the amino acid sequence shown below (SEQ ID NO: 1). The peptide-N of the present invention was designed on the basis of the amino acid sequence that exists on the N-terminus side of the sheathlin protein.

X01 Pro X02 X03 X04 X05 X06 X07 X08 X09 X10 X11 X12 X13 X14 X15 X16 X17 X18 X19 X20

In the above amino acid sequence, X01 to X20 represent the following amino acid residues.
X01: Val or Gln
X02: Ala, Phe or Gly
X03: Phe or Leu
X04: Pro or Lys
X05: Arg, Gln or Pro
X06: Gln, Arg or Phe
X07: Pro, Ser or Leu
X08: Absence of amino acid residue, or Gly or Gln
X09: Absence of amino acid residue, or Ala, Gly or Pro
X10: Absence of amino acid residue, or Gln or Thr
X11: Absence of amino acid residue, or Gly or Ala
X12: Absence of amino acid residue, or Met or Ala
X13: Gly, Ala or Thr
X14: Thr, Ile, Pro or Gly
X15: Pro or Val
X16: Gly or Gln
X17: Val, Met or Gly
X18: Ala or Thr
X19: Ser or Pro
X20: Leu or Gln Peptides having the following amino acid sequence (SEQ ID NO: 2) fall within the scope of the peptide-N of the present invention:

Val Pro X21 Phe Pro X22 Gln X23 Gly X24 Pro Gly X25 Ala Ser Leu

In the above amino acid sequence, X21 to X25 represent the following amino acid residues.
X21: Ala or Phe
X22: Arg or Gln
X23: Pro or Ser
X24: Thr or Ile
X25: Val, Met or Gly Specifically, the peptide-N of the present invention is preferably a peptide having any of the following amino acid sequences (A) to (G).

```
(A) Val Pro Ala Phe Pro Arg Gln Pro Gly Thr Pro Gly Val Ala    (SEQ ID NO: 3)
    Ser Leu (B) Val Pro Phe Phe Pro Gln Gln Ser Gly Thr Pro Gly Met Ala    (SEQ ID NO: 4)
    Ser Leu (C) Val Pro Ala Phe Pro Gln Gln Pro Gly Ile Pro Gly Met Ala    (SEQ ID NO: 5)
    Ser Leu (D) Val Pro Ala Phe Pro Gln Gln Pro Gly Ala Gln Gly Met Ala    (SEQ ID NO: 6)
    Pro Pro Gly Met Ala Ser Leu (E) Val Pro Ala Phe Pro Gln Arg Pro Gly Gly Gln Gly Met Ala    (SEQ ID NO: 7)
    Pro Pro Gly Met Ala Ser Leu (F) Gln Pro Gly Leu Lys Pro Phe Leu Gln Pro Thr Ala Ala Thr    (SEQ ID NO: 8)
    Gly Val Gln Val Thr Pro Gln (G) Val Pro Phe Phe Pro Gln Gln Ser Gly Thr Pro Gly Gly Ala    (SEQ ID NO: 9)
    Ser Leu
```

(2) Peptide-C of the Present Invention

The peptide-C of the present invention is a peptide having the amino acid sequence shown below (SEQ ID NO: 13). The peptide-C of the present invention was designed on the basis of an amino acid sequence that exists on the C-terminus side of the sheathlin protein.

Asn Lys X26 X27 X28 Pro X28 X29 X30 X31 X32 Ala Trp X31 Phe

In the above amino acid sequence, X26 to X32 represent the following amino acid residues.
X26: Ala or Val
X27: Gln or His
X28: Gln or Glu
X29: Ile, Met or Val
X30: Absence of amino acid residue, or Lys or Met
X31: Arg or His
X32: Asp or Asn The peptide-C of the present invention is preferably a peptide having the following amino acid sequence (SEQ ID NO: 14).

Asn Lys Ala Gln X33 Pro X33 X34 X35 X36 Asp Ala Trp X36 Phe

In the above amino acid sequence, X33 to X36 represent the following amino acid residues.
X33: Gln or Glu
X34: Ile or Met
X35: Lys or Met
X36: Arg or His Specifically, the peptide-C of the present invention is preferably a peptide having any of the following amino acid sequences (H) to (K).

```
(H) Asn Lys Ala Gln Gln Pro Gln Ile Lys Arg Asp Ala Trp Arg   (SEQ ID NO: 10)
    Phe (I) Asn Lys Ala Gln Glu Pro Glu Met Met His Asp Ala Trp His   (SEQ ID NO: 15)
    Phe (J) Asn Lys Ala Gln Gln Pro Gln Ile Lys His Asp Ala Trp His   (SEQ ID NO: 16)
    Phe (K) Asn Lys Val His Gln Pro Gln Val His Asn Ala Trp Arg Phe   (SEQ ID NO: 17)
```

(3) Production of Peptide of the Present Invention

Since the amino acid sequence of the peptide of the present invention is disclosed by the present invention, the peptide of the present invention can be produced on the basis of that sequence by a known chemical synthesis method for peptides (e.g., liquid-phase synthesis method, solid-phase synthesis method and so forth, refer to Izumiya N, Kato T. Aoyagi H, Waki M, "Basics and experiments of peptide synthesis", 1985, Maruzen). For example, in the case of producing a peptide having the aforementioned amino acid sequence (A) (SEQ ID NO: 3) by the solid-phase synthesis method, since the C-terminus (16th position) of the amino acid sequence is a leucine residue, the peptide having the aforementioned amino acid sequence (A) (SEQ ID NO: 3) can be produced by binding a carboxyl group of an α-amino group (Nα)-protected-leucine to an insoluble resin having chloromethyl group or oxymethyl group directly or via a spacer as the case may be, then removing the Nα-protective group, successively binding the 15th to the 1st amino acid residues of the amino acid sequence using corresponding protected amino acids (amino acid of which Nα-and side-chain functional group are protected is simply referred to as a "protected amino acid") according to the solid-phase synthesis method, and subsequently removing the insoluble resin and protective groups of Nα-and side-chain functional groups of the amino acid residues.

The insoluble resin having chloromethyl group or oxymethyl group, spacer used for synthesis of the peptide of the present invention, protected amino acid resin comprising a protected amino acid bound to the insoluble resin used as the case may be and so forth can be prepared by known methods, and those of various types are commercially available.

The aforementioned insoluble resin may be any resin that can bind to a carboxyl group of a protected amino acid at the C terminus directly or via a spacer as the case may be and can be removed thereafter. Preferred examples of such an insoluble resin include a chloromethyl resin (chloromethylated styrene/divinylbenzene copolymer), oxymethyl resin and 4-oxymethyl-Pam (phenylacetamidomethyl)-resin introduced with a spacer for the Boc (t-butyloxycarbonyl) strategy, oxymethylphenoxymethyl resin (Wang resin), derivatives of thereof and so forth for the Fmoc (9-fluorenylmethyloxycarbonyl) strategy.

A protected amino acid is an amino acid of which functional group is protected with a protective group by a known method, and various types of protected amino acids are commercially available.

A protected amino acid can be bound by a usual condensation method such as the DCC (dicyclohexylcarbodiimide) method, DIPCDI (diisopropylcarbodiimide) method [Tartar A et al., J. Org. Chem., 44, 5000 (1979)], active ester method, mixed or symmetric anhydride method, carbonyldiimidazole method, DCC-HONSu (N-hydroxysuccinimide) method [Weygand F et al., Z. Naturforsch., B, 21, 426 (1966)], DCC-HOBt (1-hydroxybenzotriazole) method [Koenig W et al., Chem. Ber., 103, 788, 2024, 2034 (1970)], diphenylphosphorylazide method, BOP-HOBt method using a BOP reagent (benzotriazolyl-N-hydroxy-trisdimethylaminophosphonium hexafluorophosphate) (Hudson D, J. Org. Chem., 53, 617 (1988)), HBTU (2-(1H-benzotriazol-1-yl)-1,1,3,3-tetramethyluronium hexafluorophosphate)-HOBt method (Knorr R et al., Tetrahedron Lett., 30, 1927 (1989)) and TBTU (2-(1H-benzotriazol-1-yl)-1,1,3,3-tetramethyluronium tetrafluoroborate)-HOBt method (Knorr, R. et al., Tetrahedron Lett., 30, 1927 (1989)). Among these, the DCC method, DCC-HOBt method, BOP-HOBt method, HBTU-HOBt method and symmetric anhydride method are preferred.

These condensation reactions are usually performed in an organic solvent such as dichloromethane, dimethylformamide (DMF) or N-methylpyrrolidone (NMP), or a mixed solvent thereof.

As a removing reagent for the protective group of α-amino group, trifluoroacetic acid/dichloromethane, HCl/dioxane, piperidine/DMF, piperidine/NMP and so forth are used, and the regent can be suitably selected depending on the type of the protective group.

Further, progression extent of the condensation reaction at each stage of the synthesis can be examined by the method of Kaiser et al. [Anal. Biochem., 34, 595 (1970), ninhydrin reaction method].

Thus, a protected peptide resin having a desired amino acid sequence can be obtained.

A protected peptide resin and a protective group can be simultaneously removed by treating the resin with hydrogen fluoride, TFMSA (trifluoromethanesulfonic acid) [Ed. by Gross E, Yajima H et al., "The Peptides" 5, 65 (1983), Academic Press], TMSOTf (trimethylsilyl triflate) [Fujii N et al., J. Chem. Soc., Chem. Commun., 274 (1987)], TMSBr (trimethylsilyl bromide) [Fujii N et al., Chem. Pharm. Bull., 35, 3880 (1987)], trifluoroacetic acid or the like. The aforementioned removing agent can be suitably selected depending on the used strategy (Boc or Fmoc) and the types of the resin and the protective group. The peptide of the present invention can be produced by these series of methods.

Further, the peptide of the present invention can also be produced by producing a polynucleotide (DNA or RNA) corresponding to the amino acid sequence of the peptide of the present invention and employing a genetic engineering technique using the polynucleotide.

The produced peptide can be purified by isolation and purification methods for proteins generally known in the field of protein chemistry. Specific examples include extraction, recrystallization, salting out using ammonium sulfate, sodium sulfate or the like, centrifugation, dialysis, ultrafiltration, absorption chromatography, ion exchange chromatography, hydrophobic chromatography, normal phase chromatography, reverse phase chromatography, gel filtration chromatography, gel permeation chromatography, affinity chromatography, electrophoresis, countercurrent distribution and so forth and arbitrary combinations thereof, and a method using reverse phase high performance liquid chromatography is effective.

The amino acid composition of the produced peptide of the present invention can be examined by a known method after hydrolysis of the peptide with an acid such as hydrochloric acid or methanesulfonic acid, and whether the peptide of the present invention has been correctly produced or not can be estimated by such examination.

More strictly, whether the peptide of the present invention has been correctly produced or not can be confirmed by determining the amino acid sequence of the produced peptide by a known amino acid sequencing method (e.g., Edman degradation method etc).

The peptide in the form of a salt also falls within the scope of the present invention. As described later, because the peptide of the present invention is also useful for use as a pharmaceutical, salts of the peptide of the present invention are preferably medically acceptable salts.

The peptide of the present invention can form a salt by addition of an acid. Examples of such a salt include, for example, salts with an inorganic acid (hydrochloric acid, hydrobromic acid, phosphoric acid, nitric acid, sulfuric acid and so forth) or organic carboxylic acid (acetic acid, propionic acid, maleic acid, succinic acid, malic acid, citric acid, tartaric acid, salicylic acid, trifluoroacetic acid etc.), acidic saccharide such as glucuronic acid, galacturonic acid, gluconic acid and ascorbic acid, acidic polysaccharide such as hyaluronic acid, chondroitin sulfate, heparan sulfate, heparin, 6-O-desulfated heparin, 2-O-desulfated heparin, N-desulfated heparin and alginic acid, organic sulfonic acid (methanesulfonic acid, p-toluenesulfonic acid etc.) and so forth. Among these salts, medically acceptable salts are preferred.

Further, the peptide of the present invention can form a salt with a basic substance. Examples of such a salt include medically acceptable salts among salts with an inorganic base such as alkali metal salts (sodium salts, lithium salts, potassium salts etc.), alkaline earth metal salts and ammonium salts, and salts with an organic base such as diethanolamine salts and cyclohexylamine salts.

Further, a peptide obtained by modifying the peptide of the present invention also fall within the scope of the peptide of the present invention. Examples of such a peptide include a peptide of which α-amino group or α-carboxyl group is modified, peptide of which side-chain functional group is modified and so forth. Examples of the modification include modification with a modification group or protective group commonly used in the field of peptide chemistry, replacement with a D-amino acid, which is an optical isomer, and so forth.

The relationship of the aforementioned amino acid sequences (A) to (G) among the peptides-N of the present invention is shown in Table 1. Further, the relationship of the aforementioned amino acid sequences (H) to (K) among the peptides-C of the present invention is shown in Table 2. Amino acid residues are represented by using single letter codes. Further, "-" in the amino acid sequences indicates absence of amino acid residue. For example, as for (A), it is indicated that the 8th amino acid residue is "P," and this bound to the 9th amino acid residue (G) via a peptide bond to form a peptide comprising 16 amino acid residues as a whole. Further, the animals having sheathlin molecules having each amino acid sequence (origins) are also shown.

TABLE 1

| | | |
|---|---|---|
| (A) VPAFPRQP-----GTPGVASL | (SEQ ID NO: 3) | Swine |
| (B) VPFFPQQS-----GTPGMASL | (SEQ ID NO: 4) | Human |
| (C) VPAFPQQP-----GIPGMASL | (SEQ ID NO: 5) | Bovine |
| (D) VPAFPQQPGAQGMAPPGMASL | (SEQ ID NO: 6) | Mouse, rat |
| (E) VPAFPQRPGGQGMAPPGMASL | (SEQ ID NO: 7) | Rat |
| (F) QPGLKPFLQPTAATGVQVTPQ | (SEQ ID NO: 8) | Rat |
| (G) VPFFPQQS-----GTPGGASL | (SEQ ID NO: 9) | |

TABLE 2

| | | | |
|---|---|---|---|
| (H) | NKAQQPQIKRDAWRF | (SEQ ID NO: 10) | Swine |
| (I) | NKAQEPEMMHDAWHF | (SEQ ID NO: 15) | Human |
| (J) | NKAQQPQIKHDAWHF | (SEQ ID NO: 16) | Bovine |
| (K) | NKVHQPQV-HNAWRF | (SEQ ID NO: 17) | Mouse, rat |

As shown in the examples described later, because the peptide of the present invention has an effect of promoting cell growth and effect of promoting cell differentiation, in particular, effect of promoting cell growth and effect of promoting cell differentiation for osteoblasts, periodontal cells and so forth, it can be used as an active ingredient of agents such as an agent for promoting cell growth, agent for promoting cell differentiation, agent for promoting bone or cartilage formation or regeneration, agent for promoting periodontal tissue formation or regeneration and so forth as described in detail below.

<2> Agent of the Present Invention

The agent of the present invention is an agent containing the peptide of the present invention (the peptide-N and/or peptide-C of the present invention) as an active ingredient. Although the agent of the present invention may be a pharmaceutical or a reagent for experiments or tests, it is preferably a pharmaceutical.

The agent of the present invention is preferably an agent for promoting cell growth or cell differentiation. The "cell" of which growth or differentiation is to be promoted is preferably an osteoblast, chondroblast, cementoblast, bone marrow-derived mesenchymal stem cell or periodontal ligament-derived cell. These agent for promoting cell growth and agent for promoting cell differentiation exhibit superior cell growth or cell differentiation promoting effect by the action of the peptide of the present invention as the active ingredient thereof.

Further, the agent of the present invention can also be used as an agent for promoting formation or regeneration of bone or cartilage or agent for promoting formation or regeneration of periodontal tissue by utilizing such effect of the peptide of the present invention as described above.

The peptide of the present invention used as an active ingredient of the agent of the present invention is the same as described in the aforementioned "<1> Peptide of the present invention."

Peptides having any of the following amino acid sequences (A) to (G) are particularly preferred.

```
(A) Val Pro Ala Phe Pro Arg Gln Pro Gly Thr Pro Gly Val Ala  (SEQ ID NO: 3)
    Ser Leu (B) Val Pro Phe Phe Pro Gln Gln Ser Gly Thr Pro Gly Met Ala  (SEQ ID NO: 4)
    Ser Leu (C) Val Pro Ala Phe Pro Gln Gln Pro Gly Ile Pro Gly Met Ala  (SEQ ID NO: 5)
    Ser Leu (D) Val Pro Ala Phe Pro Gln Gln Pro Gly Ala Gln Gly Met Ala  (SEQ ID NO: 6)
    Pro Pro Gly Met Ala Ser Leu (E) Val Pro Ala Phe Pro Gln Arg Pro Gly Gly Gln Gly Met Ala  (SEQ ID NO: 7)
    Pro Pro Gly Met Ala Ser Leu (F) Gln Pro Gly Leu Lys Pro Phe Leu Gln Pro Thr Ala Ala Thr  (SEQ ID NO: 8)
    Gly Val Gln Val Thr Pro Gln (G) Val Pro Phe Phe Pro Gln Gln Ser Gly Thr Pro Gly Gly Ala  (SEQ ID NO: 9)
    Ser Leu
```

Peptides having the amino acid sequence (A), (B) or (G) are particularly preferred.

Further, peptides having any of the following amino acid sequences (H) to (K) are also preferred.

```
(H) Asn Lys Ala Gln Gln Pro Gln Ile Lys Arg Asp Ala Trp Arg  (SEQ ID NO: 10)
    Phe (I) Asn Lys Ala Gln Glu Pro Glu Met Met His Asp Ala Trp His  (SEQ ID NO: 15)
    Phe (J) Asn Lys Ala Gln Gln Pro Gln Ile Lys His Asp Ala Trp His  (SEQ ID NO: 16)
    Phe (K) Asn Lys Val His Gln Pro Gln Val His Asn Ala Trp Arg Phe  (SEQ ID NO: 17)
```

Peptides having the amino acid sequence (H) or (I) are particularly preferred.

The peptide of the present invention constituting the agent of the present invention may consist of a single type of peptide or two or more types of peptides.

Purity of the peptide of the present invention as the active ingredient of the agent of the present invention can be suitably selected depending on the purpose of the agent of the present invention. For example, when the agent of the present invention is used as a pharmaceutical, preferably used is the peptide of the present invention purified to high purity and thus substantially not containing substances of which contamination is not acceptable in a pharmaceutical.

When the agent of the present invention is used as a pharmaceutical, administration route thereof can be suitably selected depending on the purpose from, for example, injection (subcutaneous, intracutaneous, intravenous, intraperitoneal injections etc.), instillation, infusion, implant, percutaneous administration, oral administration and inhalation. Further, dosage form thereof can be suitably selected from, for example, injection (solution, suspension, emulsion, solid to be dissolved upon use etc.), tablet, capsule, granule, powder, solution, liposome-encapsulated agent, ointment, gel, powder for external use, spray, powder for inhalation, eye drop, eye ointment, suppository, pessary and so forth and prepared depending on the administration method.

When the agent of the present invention is used as a pharmaceutical, the endotoxin concentrations thereof is preferably 0.3 EU/mL or lower as an agent in the form of a solution. The endotoxin concentration can be determined by using an endotoxin measurement method well known to and commonly used by those skilled in the art, and the *Limulus* test using *Limulus amebocyte* lysate is preferred. Concentrations in terms of EU (endotoxin unit) can be measured and calculated according to the Japan Industrial Standard, General rules for biochemical reagents (JIS K8008), US Pharmacopoeia or the like.

Further, other pharmaceutically active ingredients (e.g., hyaluronic acid) or ingredients usually used for pharmaceuticals such as conventional stabilizers, emulsifiers, osmotic regulators, pH modifiers, buffers, isotonic agents, preservatives, soothing agents, coloring materials, excipients, binders, lubricants and disintegrating agents can be used for the agent of the present invention so long as the peptide of the present invention and the effect of the present invention are not adversely affected.

When the agent of the present invention is used as a pharmaceutical, the dose should be selected for an individual case depending on the purpose of administration (prophylactic treatment, maintenance (prevention of exacerbation), amelioration (improvement of symptoms) or therapeutic treatment), type of disease, symptoms, sex, age and body weight of patients, application site, administration method and so forth and is not particularly limited. However, for an adult, 1 pg to 30 mg of the peptide of the present invention per application site can be generally administered at one time. Further, the administration frequency may be, for example, about once in a day or 2 to 3 times in a day for divided dose, or about once in 1 to 3 days.

When the agent of the present invention is used as a pharmaceutical, the subject administered with it is not particularly limited, but is preferably a vertebrate, more preferably a mammal, particularly preferably a human.

When the agent of the present invention is used as a pharmaceutical, it can be administered to, for example, animals or humans described below depending on the use.

When the agent of the present invention is used as an agent for promoting cell growth, it can be administered to an animal in a condition that cell growth is desired. In particular, it is preferably administered to an animal in a condition that growth of osteoblasts, chondroblasts, cementoblasts, bone marrow-derived mesenchymal stem cells or periodontal ligament-derived cells is desired. Examples of such a condition that cell growth is desired include suffering from periodontal diseases, bone fracture, bone loss, osteoporosis, articular diseases, orthopedic diseases (osteochondritis dissecans, gonarthrosis etc.), tumor or the like, conditions immediately after dental treatment (periodontal treatment etc.), orthopedic treatment (cultured cell grafting, drilling of bone, osteocartilaginous pillar grafting etc.), bone grafting in tumorectomy or bone augmentation and so forth.

When the agent of the present invention is used as an agent for promoting cell differentiation, it can be administered to an animal in a condition that cell differentiation is desired. In particular, it is preferably administered to an animal in a condition that differentiation of osteoblasts, chondroblasts, cementoblasts, bone marrow-derived mesenchymal stem cells or periodontal ligament-derived cells is desired. Examples of such a condition that cell differentiation is desired are similar to those described for the aforementioned agent for promoting cell growth.

When the agent of the present invention is used as an agent for promoting bone or cartilage formation or regeneration, it can be administered to an animal in a condition that promotion of bone or cartilage formation or regeneration is desired. Examples of such a condition that promotion of bone or cartilage formation or regeneration is desired are similar to those described for the aforementioned agent for promoting cell growth.

When the agent of the present invention is used as an agent for promoting periodontal tissue formation or regeneration, it can be administered to an animal in a condition that promotion of periodontal tissue formation or regeneration is desired. Examples of such a condition that promotion of periodontal tissue formation or regeneration is desired are similar to those described for the aforementioned agent for promoting cell growth.

Further, the peptide of the present invention may be adhered to a surface of an appropriate insoluble carrier or mixed with an appropriate material to form an agent for the purpose of promoting cell growth or cell differentiation, promoting formation or regeneration of bone, cartilage tissue or periodontal tissue, improving biocompatibility or the like. As such an insoluble carrier or material, those in various forms such as bead, film, plate, monofilament, non-woven fabric, sponge, textile, knit, short fiber, tube, and hollow fiber can be used. Specifically, the peptide of the present invention can be used for a medical composite material such as implant, bone cement, bone substitute, root canal filling material, bone fracture plate, artificial joint and so forth. The peptide of the present invention can also be applied for agents in the field of regenerative medicine.

When the peptide of the present invention is adhered to a surface of such materials, the adhesion method is not particularly limited, and methods commonly used as methods for preparing immobilized enzymes such as methods utilizing physical adsorption, ionic bond, covalent bond or entrapment (see Immobilized Enzyme, 1975, pp. 9 to 75, Kodansha) can be used.

For example, the peptide of the present invention can be physically adhered to a polystyrene or polypropylene type insoluble carrier. Further, the peptide of the present invention can be chemically adhered to, for example, a polyamide, cellulose, agarose, polyacrylamide, dextran or vinyl polymer type insoluble carrier. Examples of chemical adhesion (bonding) methods include the diazotization method, in which diazocoupling is carried out by utilizing an aromatic amino group of an insoluble carrier, the CNBr method, in which a hydroxyl group of an insoluble carrier is activated by CNBr to form a peptide bond, the acid azide method, in which a peptide bond is formed by using a hydrazine derivative of an insoluble carrier or the like, the alkylation method, in which a peptide is alkylated by utilizing a highly reactive functional group of an insoluble carrier such as a halogen, a method of crosslinking an insoluble carrier and a free amino group of a peptide by using a crosslinking reagent that reacts with a free amino group such as glutaraldehyde, the carbodiimide method, the epoxy activation method, a method of binding the peptide via a spacer by using any of these methods and so forth. The method for binding the peptide of the present invention can be suitably selected from these known methods depending on the type of the insoluble carrier.

Further, when the agent of the present invention is used as a reagent for experiments or tests, the peptide of the present invention may be used as it is or as a mixture with other ingredients depending on the use.

<3> Composition of the Present Invention

The composition of the present invention is characterized by containing at least the peptide of the present invention (the peptide-N and/or peptide-C of the present invention) and hyaluronic acid or a pharmaceutically acceptable salt thereof.

The peptide of the present invention as a constituent of the composition of the present invention is the same as described in the aforementioned "<1> Peptide of the present invention."

Peptides having any of the following amino acid sequences (A) to (G) are particularly preferred.

```
(A) Val Pro Ala Phe Pro Arg Gln Pro Gly Thr Pro Gly Val Ala    (SEQ ID NO: 3)
    Ser Leu (B) Val Pro Phe Phe Pro Gln Gln Ser Gly Thr Pro Gly Met Ala    (SEQ ID NO: 4)
    Ser Leu (C) Val Pro Ala Phe Pro Gln Gln Pro Gly Ile Pro Gly Met Ala    (SEQ ID NO: 5)
    Ser Leu
```

```
                           -continued
(D) Val Pro Ala Phe Pro Gln Gln Pro Gly Ala Gln Gly Met Ala    (SEQ ID NO: 6)
    Pro Pro Gly Met Ala Ser Leu (E) Val Pro Ala Phe Pro Gln Arg Pro Gly Gly Gln Gly Met Ala    (SEQ ID NO: 7)
    Pro Pro Gly Met Ala Ser Leu (F) Gln Pro Gly Leu Lys Pro Phe Leu Gln Pro Thr Ala Ala Thr    (SEQ ID NO: 8)
    Gly Val Gln Val Thr Pro Gln (G) Val Pro Phe Phe Pro Gln Gln Ser Gly Thr Pro Gly Gly Ala    (SEQ ID NO: 9)
    Ser Leu
```

Peptides having the amino acid sequence of (A), (B) or (G) are particularly preferred.

Further, peptides having any of the following amino acid sequences (H) to (K) are also preferred.

```
(H) Asn Lys Ala Gln Gln Pro Gln Ile Lys Arg Asp Ala Trp Arg    (SEQ ID NO: 10)
    Phe (I) Asn Lys Ala Gln Glu Pro Glu Met Met His Asp Ala Trp His    (SEQ ID NO: 15)
    Phe (J) Asn Lys Ala Gln Gln Pro Gln Ile Lys His Asp Ala Trp His    (SEQ ID NO: 16)
    Phe (K) Asn Lys Val His Gln Pro Gln Val His Asn Ala Trp Arg Phe    (SEQ ID NO: 17)
```

Peptides having the amino acid sequence of (H) or (I) are particularly preferred.

The peptide of the present invention constituting the composition of the present invention may consist of a single type of peptide or two or more types of peptides.

The origin of the "hyaluronic acid or a pharmaceutically acceptable salt thereof" as a constituent of the composition of the present invention is not particularly limited. For example, any of hyaluronic acids isolated and purified from chicken crest, umbilical cord, microorganisms producing hyaluronic acid and so forth, and hyaluronic acid produced by synthesis (e.g., chemical synthesis or enzymatic synthesis) can be used. The molecular size of hyaluronic acid is not particularly limited. For example, hyaluronic acid having a weight average molecular weight of 600,000 to 1,200,000 is exemplified. For example, hyaluronic acid having a molecular weight of about 800,000 to 1,000,000 is a preferred example.

As the "pharmaceutically acceptable salt" of hyaluronic acid, pharmaceutically acceptable salts among salts with an inorganic base such as alkali metal salts (sodium salts, lithium salts, potassium salts etc.), alkaline earth metal salts and ammonium salts and salts with an organic base such as diethanolamine salts, cyclohexylamine salts and amino acid salts can be used. Among these, sodium salts are preferred.

The composition of the present invention can be produced by appropriately mixing the peptide of the present invention and such "hyaluronic acid or a pharmaceutically acceptable salt thereof." The mixing ratio (content ratios in the composition) of these ingredients is not particularly limited, either. The expression "containing at least the peptide of the present invention and hyaluronic acid or a pharmaceutically acceptable salt thereof" encompasses use of hyaluronic acid addition salts as the peptide of the present invention.

The composition of the present invention may be in any of solution, frozen or dried (lyophilized etc.) form.

The content of impurities and so forth in the composition of the present invention can also be suitably defined depending on purpose of use and are not particularly limited. However, it is preferred that the composition does not substantially contain substances of which contamination is not acceptable in pharmaceuticals.

For example, the endotoxin concentration in the composition of the present invention is preferably 0.3 EU/mL or lower, as a solution. The endotoxin concentration in the composition of the present invention can be measured and calculated by an endotoxin measurement method well known to and conventionally used by those skilled in the art as described above. Further, the iron content is preferably 20 ppm or less.

Further, in the composition of the present invention, so long as the peptide of the present invention and the effect of the present invention are not adversely affected, other pharmaceutically active ingredients (e.g., hyaluronic acid) or ingredients commonly used for pharmaceuticals such as conventional stabilizers, emulsifiers, osmotic regulators, pH modifiers, buffers, isotonic agents, preservatives, soothing agents, coloring materials, excipients, binders, lubricants and disintegrating agents can also be used.

Such a composition of the present invention is preferably used for medical use.

When the composition of the present invention is used as a pharmaceutical, it can be used for the same purposes as those of the aforementioned agent of the present invention used as a pharmaceutical, and in particular, it is preferably used for diseases in which the peptide of the present invention needs to be retained to some extent, for example, for lesions of periodontal diseases, bone fracture, bone loss, articular diseases, orthopedic diseases etc., at the time of intervertebral fusion and so forth.

EXAMPLES

The present invention will be explained more specifically with reference to the following examples.

Example 1

Production of the Peptide of the Present Invention

The following peptides (a) to (e) were produced according to solid-phase synthesis by entrusting the production to Peptide Institute, Inc. The peptide (a) is a peptide designed on the basis of the amino acid sequence existing on the N-terminus side of a swine-derived sheathlin protein, (b) is a peptide designed on the basis of the amino acid sequence of a portion in a human-derived sheathlin protein corresponding to (a), (c) is a peptide designed on the basis of the amino acid sequence existing on the C-terminus side of the swine-derived sheathlin protein, and both (d) and (e) are peptides designed on the basis of the amino acid sequence existing in an internal region between the N-terminus side and the C-terminus side of the swine-derived sheathlin protein. The peptides (a), (b) and (c) are the peptides of the present invention.

```
(a) Val Pro Ala Phe Pro Arg Gln Pro Gly Thr Pro Gly Val Ala    (SEQ ID NO: 3)
    Ser Leu (b) Val Pro Phe Phe Pro Gln Gln Ser Gly Thr Pro Gly Met Ala    (SEQ ID NO: 4)
    Ser Leu (c) Asn Lys Ala Gln Gln Pro Gln Ile Lys Arg Asp Ala Trp Arg    (SEQ ID NO: 10)
    Phe (d) Glu His Glu Thr Gln Gln Tyr Glu Tyr Ser                    (SEQ ID NO: 11)

(e) Ala Arg Gly Pro Ala Gly Arg Ser Arg Gly Pro Pro Gly        (SEQ ID NO: 12)
```

The results of the amino acid analysis of the produced peptides (a) and (b) (hydrolysis conditions: 6 N HCl, 110° C., 22 hours) are shown below. The figures in the parentheses represent theoretical values.

Peptide (a): Thr (1) 0.94, Ser (1) 0.89, Glu (1) 1.00, Gly (2) 2.05, Ala (2) 2.07, Val (2) 2.01, Leu (1) 1.02, Phe (1) 0.99, $NH_2$ (1) 1.13, Arg (1) 0.98, Pro (4) 4.00

Peptide (b): Thr (1) 0.94, Ser (2) 1.77, Glu (2) 2.00, Gly (2) 1.97, Ala (1) 1.00, Val (1) 0.97, Met (1) 0.98, Leu (1) 0.99, Phe (2) 1.96, $NH_2$ (2) 2.12, Pro (3) 2.99

Further, the results of purity test of the produced peptides (a) and (b) (determined by high performance liquid chromatography) are shown below. Both of the peptides showed a single peak in the elution pattern of high performance liquid chromatography (reverse phase chromatography).

Peptide (a): 97.3%

Peptide (b): 96.4%

The conditions of the high performance liquid chromatography were as follows.

Column: Zorbax 300SB-C18 (4.6 mm I.D.×150 mm) (Agilent Technologies)

Eluent: 10 to 60% acetonitrile/0.1% trifluoroacetic acid (25 min)

Flow rate: 1.0 mL/min

Temperature: 25° C. for the peptide (a) and 50° C. for the peptide (b)

Detection wavelength: 220 nm

Further, results of the molecular weight analysis of the produced peptides (a) and (b) using electrospray ionization mass spectrometry (ESI-MS) were as follows.

Peptide (a): 1593.6 (theoretical value: 1593.8)

Peptide (b): 1663.6 (theoretical value: 1663.9)

The above results suggested that the peptides (a) and (b) had been correctly produced.

Further, the produced peptides (c) to (e) were similarly analyzed. As a result, all of them had a purity of 98.0% or higher and showed a single peak in the high performance liquid chromatography (reverse phase chromatography), and it was revealed that the results of the amino acid analysis and molecular weight analysis well agreed with the theoretical values. This suggested that the peptides (c) to (e) had also been correctly produced. All the produced peptides (a) to (e) were in the form of white lyophilized substance.

Further, peptides corresponding to the aforementioned peptide (b) a part of which was deleted (peptides (f) to (j) shown below), peptides corresponding to the aforementioned peptide (b) added with several amino acid residues to the N terminus and/or C terminus (peptides (k) to (m) shown below) and peptides corresponding to the aforementioned peptide (b) a part of which amino acid residue(s) was replaced with another amino acid residue (peptide (n) shown below) were produced by solid-phase synthesis in the same manner as described above. The peptide (n) is the peptide of the present invention.

```
(f) Val Pro Phe Phe Pro Gln Gln Ser Gly Thr Pro Gly            (SEQ ID NO: 18)

(g) Val Pro Phe Phe Pro Gln Gln Ser                            (SEQ ID NO: 19)

(h) Pro Gln Gln Ser Gly Thr Pro Gly                            (SEQ ID NO: 20)

(i) Ser Gly Thr Pro Gly Met Aia Ser Leu                        (SEQ ID NO: 21)

(j) Pro Gln Gln Ser Gly Thr Pro Gly Met Ala Ser Leu            (SEQ ID NO: 22)

(k) Met Ser Phe Ala Val Pro Phe Pro Gln Gln Ser Gly Thr        (SEQ ID NO: 23)
    Pro Gly Met Ala Ser Leu (l) Val Pro Phe Phe Pro Gln Gln Ser Gly Thr Pro Gly Met Ala    (SEQ ID NO: 24)
    Ser Leu Ser Leu Glu Thr
```

-continued (m) Phe Ala Val Pro Phe Phe Pro Gln Gln Ser Gly Thr Pro Gly  (SEQ ID NO: 25)
    Met Ala Ser Leu Ser Leu (n) Val Pro Phe Phe Pro Gln Gln Ser Gly Thr Pro Gly Gly Ala  (SEQ ID NO: 9)
    Ser Leu The produced peptides (f) to (n) were similarly analyzed. As a result, all of them had a purity of 98.0% or higher and showed a single peak in high performance liquid chromatography (reverse phase chromatography), and it was revealed that the results of the amino acid analysis and molecular weight analysis well agreed with the theoretical values. This suggested that the peptides (f) to (n) had also been correctly produced. All the produced peptides (f) to (n) were in the form of white lyophilized substance.

Example 2

Pharmacological Study Using Cells (1) Preparation of Cells
(i) Human-derived Periodontal Ligament Cells (PDL Cells)

PDL cells were isolated from a healthy premolar carefully extracted from a patient (16.24 years old) who visited a hospital to extract teeth for orthodontic treatment so that periodontal ligament should not be damaged as far as possible, and cultured. The extracted tooth was washed with sterilized physiological saline and phosphate-buffered saline (PBS, Nissui), and then periodontal ligament existing in ⅓ of the tooth root at the center was scraped off with a sharp knife. The pieces of periodontal ligament were transferred to a plastic plate and minced into small fragments using a round-blade knife. Tissue fragments were left standing in a plate having a diameter of 35 mm (FALCON) and cultured in Dulbecco's modified Eagle medium (DMEM, Nissui) containing antibiotics (100 U/ml of penicillin G, 100 µg/ml of streptomycin and 250 µg/ml of gentamicin) and 10% fetal bovine serum (FBS, EQUITECH-BIO) at 37° C. under 5% $CO_2$. Then, cells released from the periodontal ligament tissue fragments were subcultured under the same conditions, and the 3rd to 5th generation cells were used for experiments.

(ii) Mouse-derived Osteoblasts

As mouse-derived osteoblasts, cells of the MC3T3 cell strain or ST2 cell strain (purchased from Riken Cell Bank) were used.

(iii) Rat Femur Bone Marrow-derived Mesenchymal Stem Cells (BMMSC)

Rat femur bone marrow-derived mesenchymal stem cells (BMMSC) were used. The cell strain of the cells was obtained according to the method of Maniatopoulos et al. (Maniatopoulos C, Sodek J and Melcher A H, Bone formation in vitro by stromal cells obtained from bone marrow of young adult rats, Cell Tissue Res., 254: 317-330, 1988). The femur was aseptically extracted, and surrounding soft tissue was removed as far as possible. The mesiodistal epiphysis of the femur was cut off, and the femur marrow tissue in 5 ml of 15S-containing minimum essential medium alpha medium (αMEM, GIBCO) was injected into 10 ml of the same culture broth by using a syringe. The obtained tissue was cultured in the 15S-containing αMEM at 37° C., and the 3rd to 5th generation cells were used for experiments.

(iv) Mouse-derived Cementoblasts

As mouse-derived cementoblasts, cells of the OCCM30 cell strain (Bone, 1999 Jul., 25(1):39-47) were used. This cell strain was provided from Professor Somerman of School of Dentistry University of Washington.

(2) Effects of the Peptide of the Present Invention on Cell Growth

The PDL cells prepared in (1) were inoculated on a 24-well culture plate (FALCON) at a ratio of $5\times10^3$ cells/well. After the inoculation, the cells were cultured in DMEM containing 10% FBS for 1 day. On Day 0, next day of the inoculation, the peptide (a) prepared above was added to a culture medium (DMEM containing 2% FBS) at various concentrations. On Days 4 and 6, the cells were separated and dispersed by using PBS containing 0.08% trypsin and 0.04% ethylenediaminetetraacetic acid (EDTA), and cell number was counted by using a Coulter counter (COULTER Z1, Coulter Electronics).

Further, the peptide (a) and anti-SPN16 antibody (antibody that binds to the amino acid sequence of SEQ ID NO: 3 existing in a sheathlin molecule, provided by Professor Uchida of Hiroshima University) preincubated at 37° C. for 30 minutes beforehand were also similarly examined.

Further, as a control, DMEM containing 2% FBS was also similarly examined.

The results are shown in FIG. 1. In FIG. 1, the bar graph on the left shows the results on Day 4, and the bar graph on the right shows the results on Day 6. The symbol "cont" in FIG. 1 indicates the results for the cells cultured in DMEM containing 2% FBS alone, "PN" indicates the results for the cells cultured in the medium added only with the peptide (a), and "(anti)PN" indicates the results for the cells cultured in the medium added with the preincubation product of the peptide (a) and the anti-SPN16 antibody. In FIG. 1, "pg" and "ng" represent "pg/ml" and "ng/ml," respectively.

As a result, when the peptide (a) was added, the PDL cells significantly increased, and this effect was inhibited by the anti-SPN16 antibody (that binds to the peptide (a)). Thus, it was demonstrated that the peptide (a) had a cell growth promoting effect.

Figure 2:
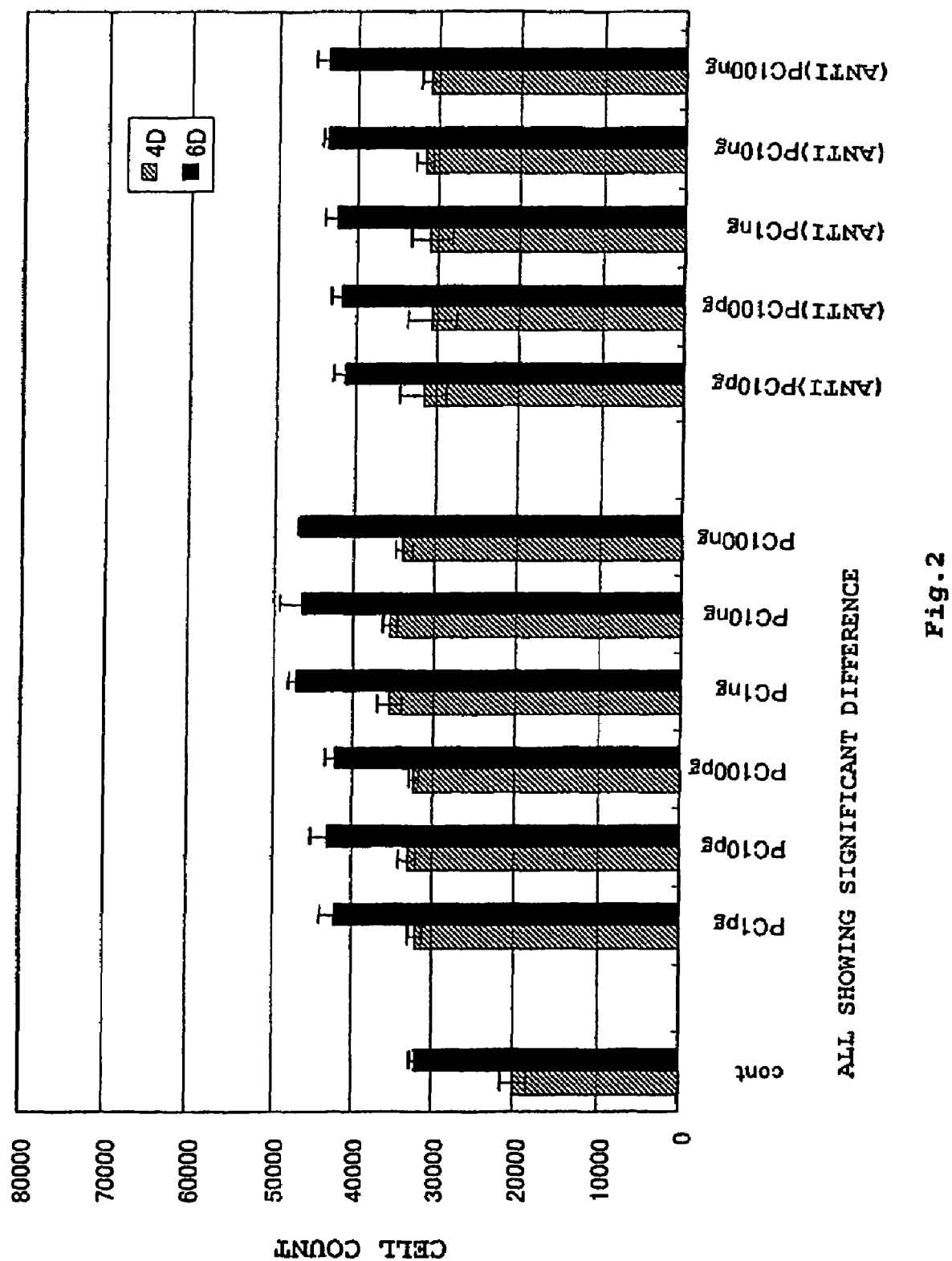
FIG. 2 shows the cell growth promoting effects of the peptide-C of the present invention (derived from swine) on the PDL cells (derived from human).

Further, the peptide (c) was also similarly examined. The results are shown in FIG. 2. In FIG. 2, the bar graph on the left shows the results on Day 4, and the bar graph on the right shows the results on Day 6. The symbol "cont" in FIG. 2 indicates the results for the cells cultured in DMEM containing 2% FBS alone, "PC" indicates the results for the cells cultured in the medium added only with the peptide (c), and "(anti)PC" indicates the results for the cells cultured in the medium added with the preincubation product of the peptide (c) and the anti-SPC15 antibody. In FIG. 2, "pg" and "ng" represent "pg/ml" and "ng/ml," respectively.

As a result, a tendency was observed that when the peptide (c) was added, the PDL cells significantly increased, and this effect was inhibited by the anti-SPC15 antibody (that binds to the peptide (c)). Therefore, it was demonstrated that the peptide (c) had a cell growth promoting effect.

Figure 3:
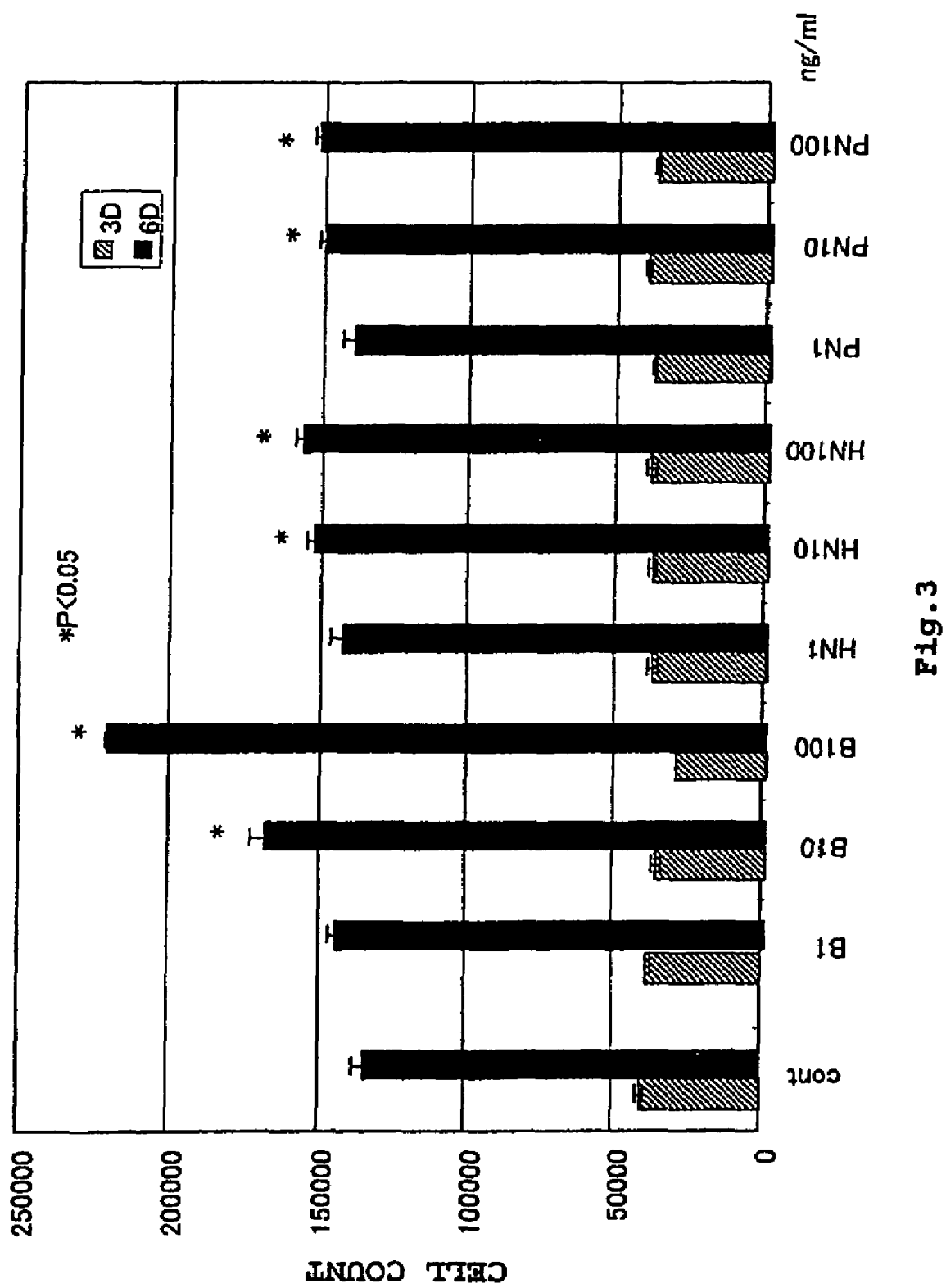
FIG. 3 shows the cell growth promoting effects of the peptides-N of the present invention (derived from swine and human) on the MC3T3 cells (derived from mouse).

Further, the peptides (a) and (b) were similarly examined for cell growth promoting effect on the MC3T3 cells. The results are shown in FIG. 3. In FIG. 3, the bar graph on the left shows the results on Day 3, and the bar graph on the right shows the results on Day 6. The symbol "cont" in FIG. 3 indicates the results for the cells cultured in αMEM containing 2% FBS alone, "B" indicates the results for the cells cultured in the medium added only with BMP2 (bone morphogenetic protein 2, Yamanouchi Pharmaceutical Co., Ltd.), "HN" indicates the results for the cells cultured in the medium added only with the peptide (b), and "PN" indicates the results for the cells cultured in the medium added with only the peptide (a). In FIG. 3, the unit of numerical values shown after "B," "HN" and "PN" is "ng/ml."

As a result, when the peptides (a) or (b) was added, the MC3T3 cells significantly increased on Day 6. Therefore, it was demonstrated that the peptides (a) and (b) had a cell growth promoting effect.

(3) Effects of the Peptide of the Present Invention on Cell Differentiation

As an index of cell differentiation, alkaline phosphatase (ALP) activity of cells was determined. Cells were inoculated in a 24-well culture plate at a ratio of $5 \times 10^3$ cells/well, added with the peptide (a) at various concentrations and cultured in DMEM or αMEM containing 2% FBS. One week after the time point when the cells reached a confluent state, ALP activity was determined by the following enzymochemical method (Bessey-Lowry method, Bessey O A, Lowry O H and Brock M J, A method for the rapid determination of alkaline phosphatase with five cubic millimeter of serum, J. Biol. Chem., 164:321-329, 1946).

(Method for Determining Alp Activity)

The cultured cells were washed with PBS and then disrupted in 10 mM Tris-HCl buffer (pH 7.4, 500 μl) for 40 seconds by using an ultrasonic homogenizer (Handy Sonic model UR-20P, Tomy Seiko) and stirred. Then, 25 μl of this sample liquid was added to 125 μl of ALP buffer (0.1 M carbonate buffer, pH 9.8, 6.7 mM p-nitrophenyl phosphate, 2 mM $MgCl_2$) and incubated at 37° C. for 30 minutes. The reaction was terminated by addition of 125 μl of 0.2 N NaOH, and absorbance was measured at 405 nm by using a microplate reader (Model 550, Bio-Rad Laboratories).

Figure 4:
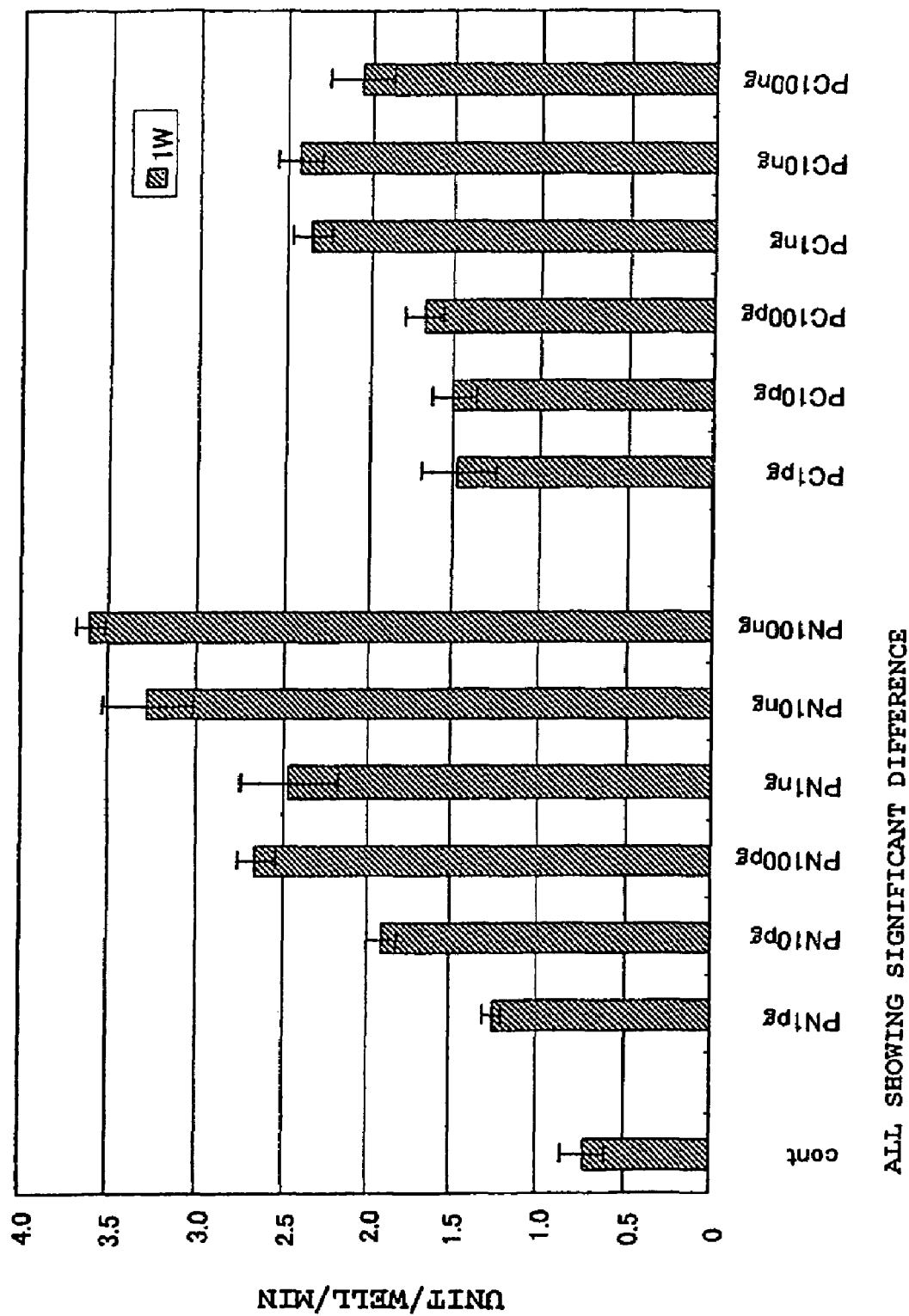
FIG. 4 shows the cell differentiation promoting effects of the peptide-N of the present invention and the peptide-C of the present invention (derived from swine) on the PDL cells (derived from human).

Further, the ALP activity in DMEM containing 2% FBS and DMEM or αMEM containing 2% FBS added with peptide (c) at various concentrations was also similarly examined. The results are shown in FIG. 4. The symbol "cont" in FIG. 4 indicates the results for the cells cultured in DMEM containing 2% FBS alone, "PN" indicates the results for the cells cultured in the medium added only with the peptide (a), and "PC" indicates the results for the cells cultured in the medium added only with the peptide (c). In FIG. 4, "pg" and "ng" represent "pg/ml" and "ng/ml," respectively.

As a result, when the peptide (a) or (c) was added, the ALP activity of the PDL cells significantly increased. Therefore, it was demonstrated that the peptides (a) and (c) had cell differentiation promoting effect.

Figure 5:
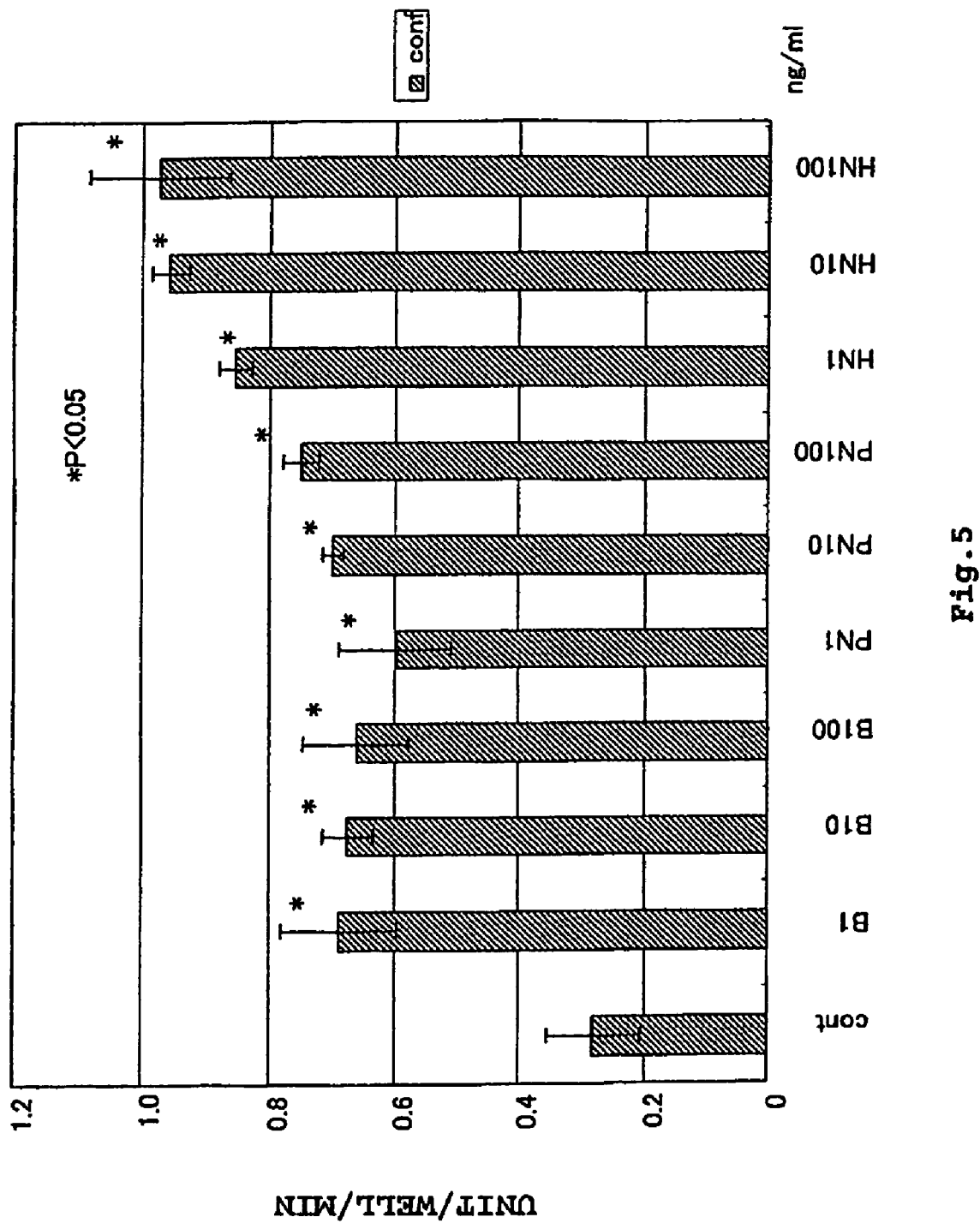
FIG. 5 shows the cell differentiation promoting effects of the peptides-N of the present invention (derived from swine and human) on the PDL cells (derived from human).
Figure 6:
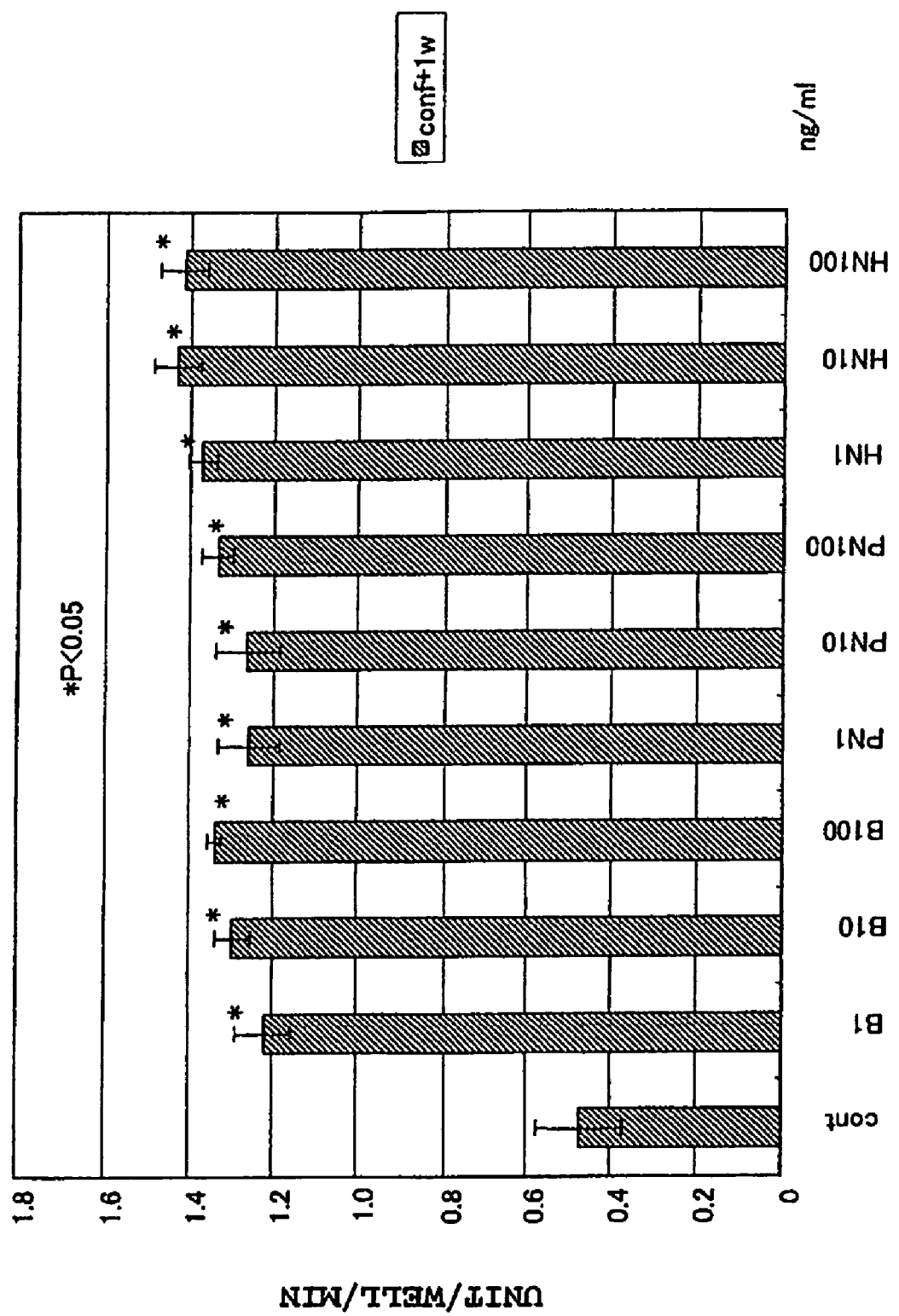
FIG. 6 shows the cell differentiation promoting effects of the peptides-N of the present invention (derived from swine and human) on the PDL cells (derived from human).

Further, in addition to the peptide (a) (derived from swine), the human-derived peptide (b) and BMP were similarly examined. The results of ALP activity measurement performed when the cells reached a confluent state are shown in FIG. 5, and the results of ALP activity measurement performed one week after the confluent state was attained are shown in FIG. 6. The symbol "cont" in the figures indicates the results for the cells cultured in DMEM containing 2% FBS alone, "B" indicates the results for the cells cultured in the medium added only with BMP2, "PN" indicates the results for the cells cultured in the medium added only with the peptide (a), and "HN" indicates the results for the cells cultured in the medium added only with the peptide (b) In the figures, the unit of numerical values shown after "B," "PN" and "HN" is "ng/ml."

As a result, when the peptide (a) or (b) was added, the ALP activity of the PDL cells significantly increased. Further, this effect was comparable to or higher than that of BMP2. These results demonstrated that the peptides (a) and (b) had an extremely high cell differentiation promoting effect.

Figure 7:
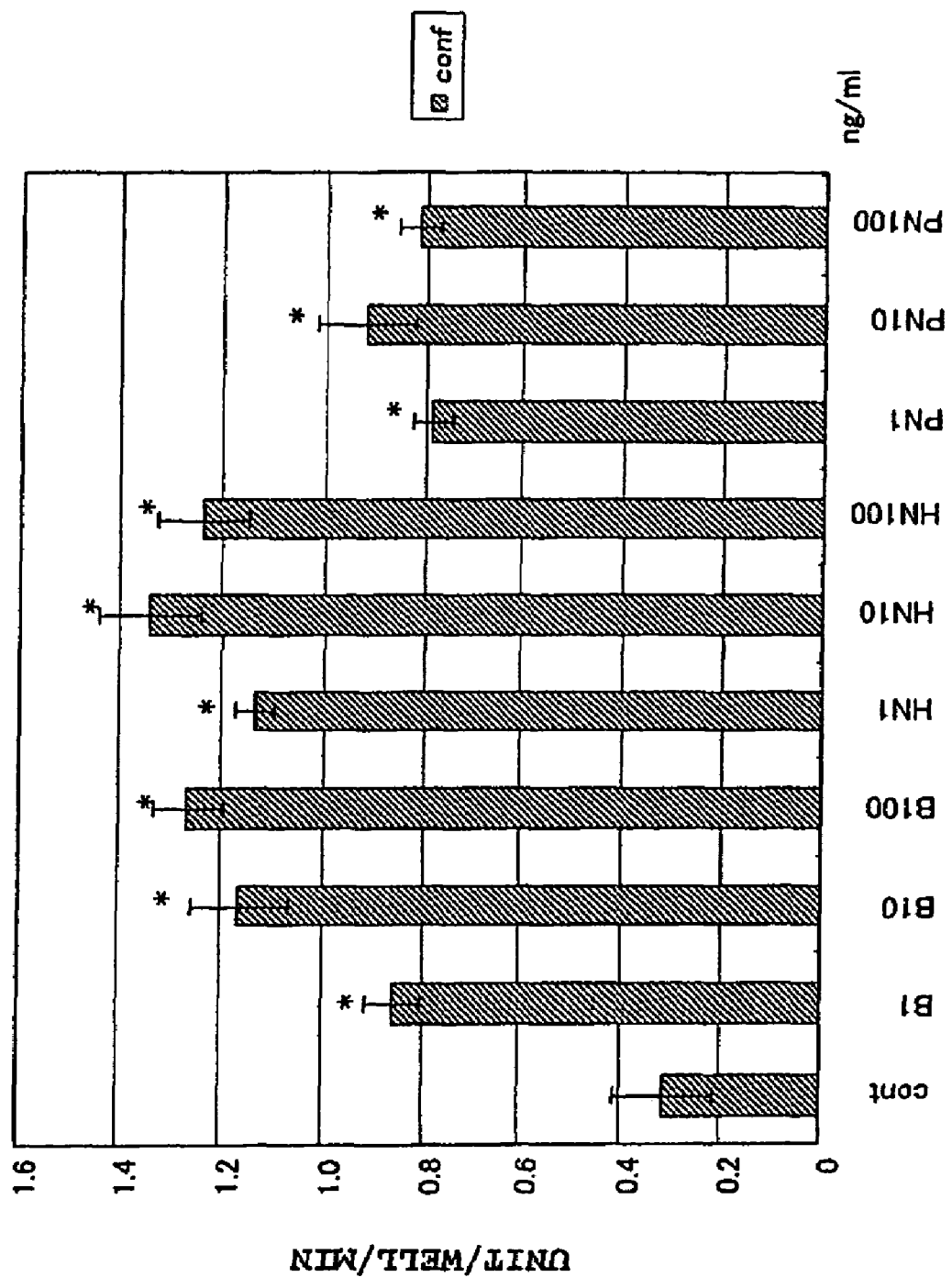
FIG. 7 shows the cell differentiation promoting effects of the peptides-N of the present invention (derived from swine and human) on the ST2 cells (derived from mouse).
Figure 8:
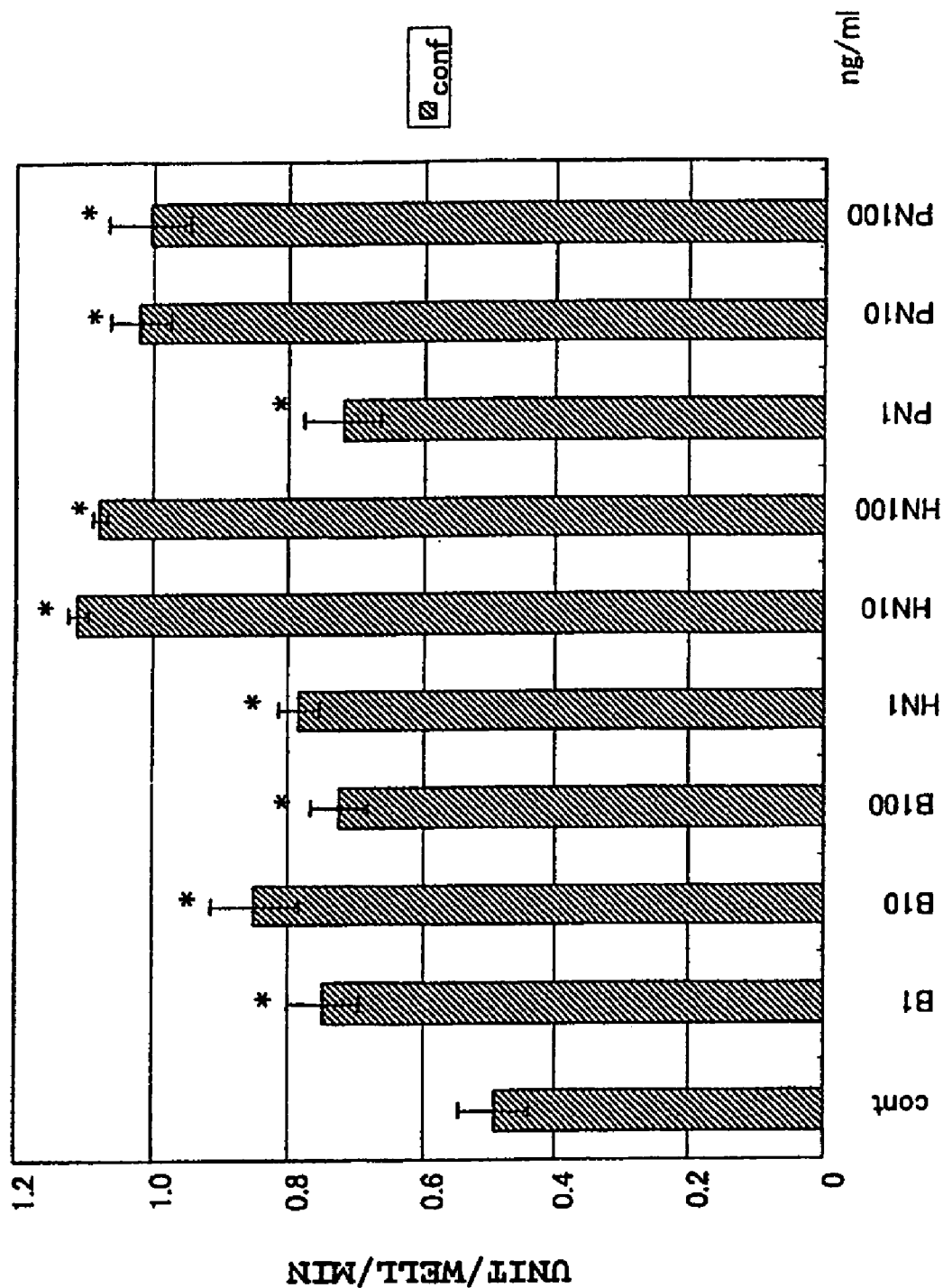
FIG. 8 shows the cell differentiation promoting effects of the peptides-N of the present invention (derived from swine and human) on the BMSSC cells (derived from rat).

Further, the peptides (a) and (b) and BMP2 were similarly examined by using the ST2 cells and BMMSC cells. ALP activities determined when the ST2 cells and BMMSC cells reached a confluent state are shown in FIGS. 7 and 8, respectively. The symbol "cont" in the figures indicates the results for the cells cultured in αMEM containing 2% FBS alone, "B" indicates the results for the cells cultured in the medium added only with BMP2, "HN" indicates the results for the cells cultured in the medium added only with the peptide (b), and "PN" indicates the results for the cells cultured in the medium added only with the peptide (a). In the figures, the unit of numerical values shown after "B," "HN" and "PN" is "ng/ml."

As a result, the peptides (a) and (b) exhibited a significant cell differentiation promoting effect not only on the PDL cells but also on the ST2 cells and BMSSC cells. Further, this effect was comparable to or higher than that of BMP2. These results also demonstrated that the peptides (a) and (b) had an extremely high cell differentiation promoting effect.

Figure 9:
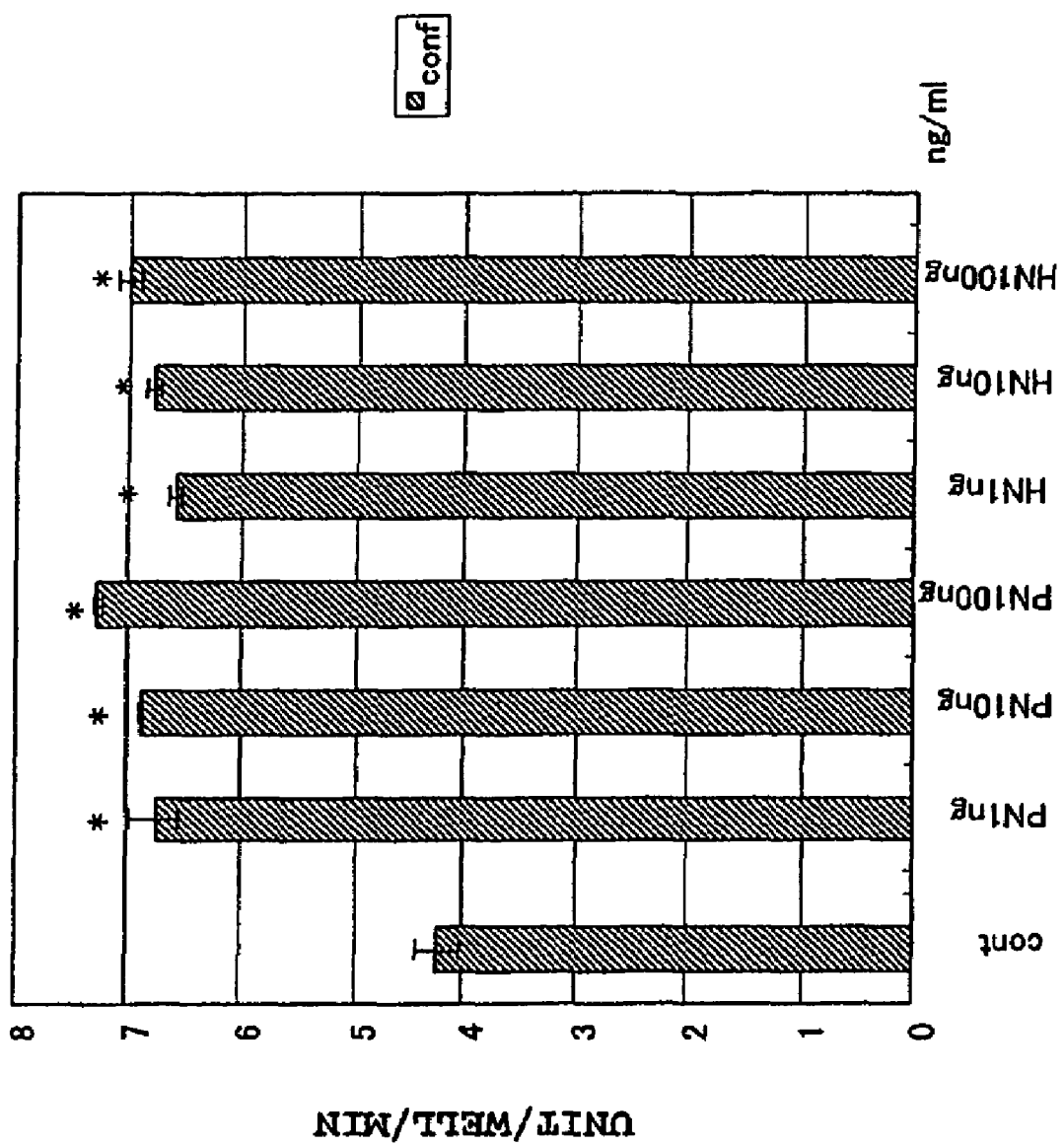
FIG. 9 shows the cell differentiation promoting effects of the peptides-N of the present invention (derived from swine and human) on the MC3T3 cells (derived from mouse).
Figure 10:
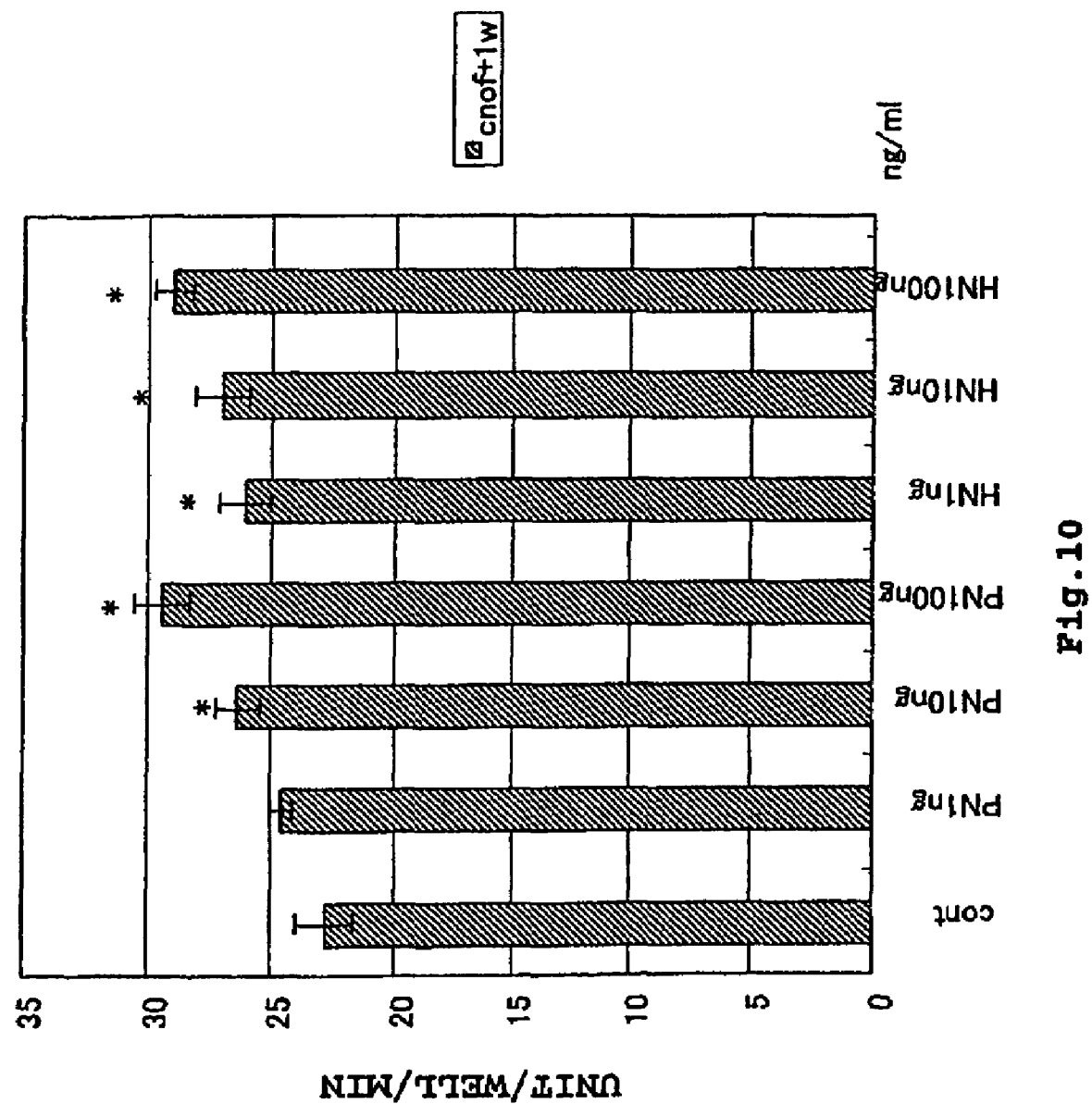
FIG. 10 shows the cell differentiation promoting effects of the peptides-N of the present invention (derived from swine and human) on the MC3T3 cells (derived from mouse).

Further, the peptides (a) and (b) were similarly examined by using the MC3T3 cells. ALP activity determined when the cells reached a confluent state is shown in FIG. 9, and ALP activity determined one week after the confluent state was attained is shown in FIG. 10. The symbol "cont" in the figures indicates the results for the cells cultured in αMEM containing 2% FBS alone, "PN" indicates the results for the cells cultured in the medium added only with the peptide (a), and "HN" indicates the results for the cells cultured in the medium added only with the peptide (b). Further, "ng" in the figures represents "ng/ml."

As a result, the peptides (a) and (b) exhibited a significant cell differentiation promoting effect on the MC3T3 cells with good reproducibility.

Figure 11:
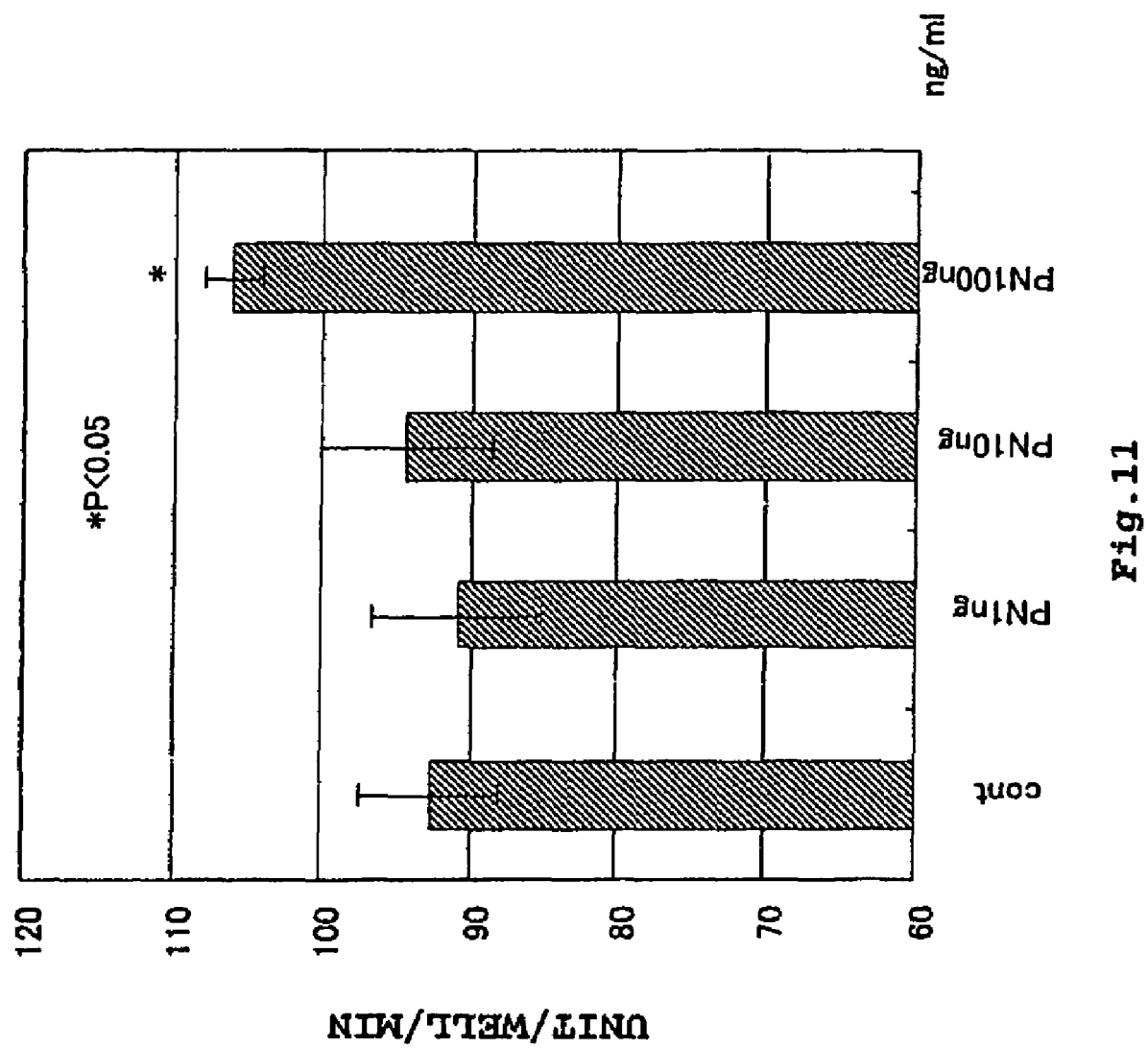
FIG. 11 shows the cell differentiation promoting effects of the peptide-N of the present invention (derived from swine) on the OCCM30 cells (derived from mouse).

Further, the peptide (a) was similarly examined by using the OCCM30 cells. The results are shown in FIG. 11. The symbol "cont" in the figure indicates the results for the cells cultured in DMEM containing 2% FBS alone, and "PN" indicates the results for the cells cultured in the medium added only with the peptide (a). Further, "ng" in the figure represents "ng/ml."

As a result, the peptide (a) exhibited a significant cell differentiation promoting effect also on the OCCM30 cells.

Figure 12:
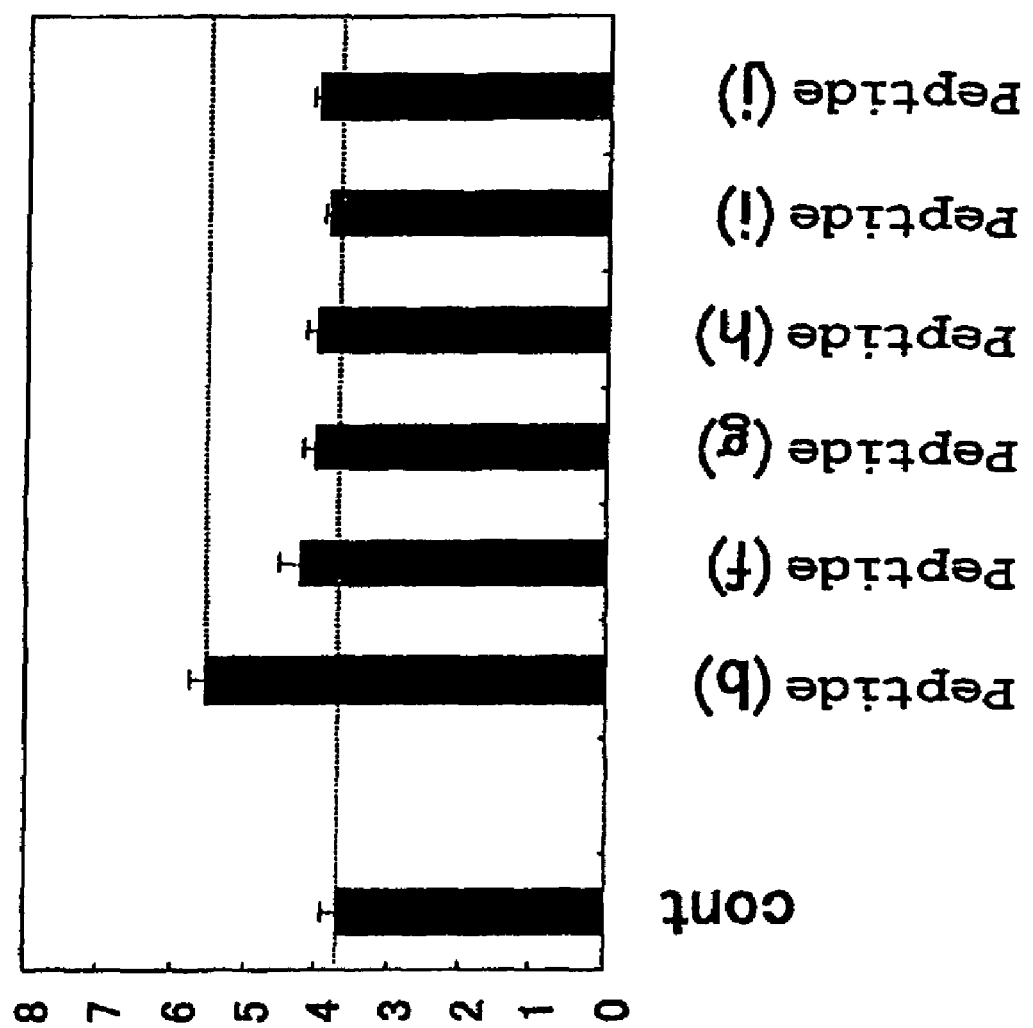
FIG. 12 shows the cell differentiation promoting effects of the peptide of the present invention (including deletion, derived from human) on the MC3T3 cells (derived from mouse).

Further, the peptides (b) and (f) to (j) were similarly examined at a final concentration of 100 ng/ml by using the MC3T3 cell strain. The results are shown in FIG. 12. The symbol "cont" in the figure indicates the results for the cells cultured in DMEM containing 2% FBS alone.

As a result, it was demonstrated that the peptide (b) exhibited a high cell differentiation promoting effect on the MC3T3 cell strain, and the peptides (f) to (j) also exhibited a higher cell differentiation promoting effect compared with the control, although the difference was small.

Figure 13:
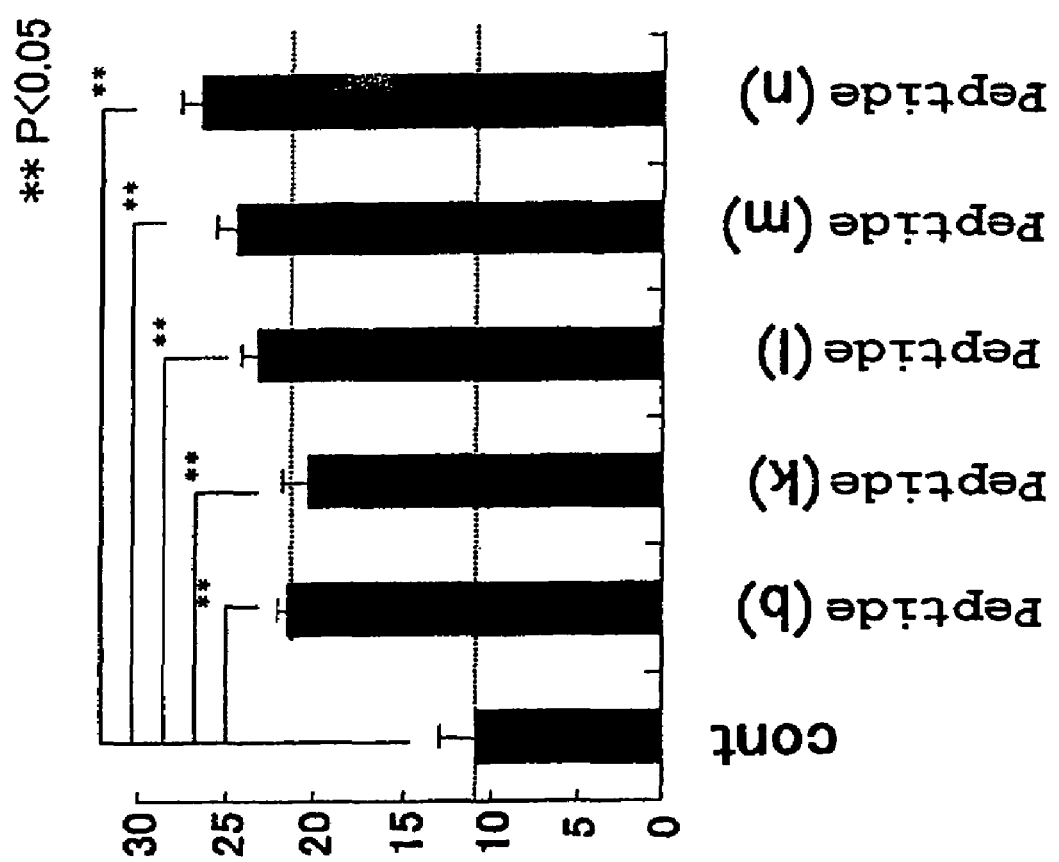
FIG. 13 shows the cell differentiation promoting effects of the peptide of the present invention (including addition or substitution of several amino acid residues, derived from human) on the ST2 cells (derived from mouse).

Further, the peptides (b) and (k) to (n) were similarly examined at a final concentration of 100 ng/ml by using the ST2 cell strain. The results are shown in FIG. 13. The symbol "cont" in the figure indicates the results for the cells cultured in DMEM containing 2% FBS alone.

As a result, it was demonstrated that all the peptides exhibited significantly high cell differentiation promoting effect on the ST2 cell strain. These results revealed that even peptides obtained by adding several amino acid residues at the N-terminus and/or C-terminus of the peptide (b) and peptides obtained by replacing a part of amino acid residues in the peptide (b) exhibited a high cell differentiation promoting effect.

(Effect of Peptide on Calcification Product Forming Ability of Cells)

The following experiment was performed to examine effect of the peptide on calcification product forming ability of cells.

To assess calcification ability of cells, Dahl's calcium staining was performed. The PDL cells were inoculated on a 24-well culture plate at a ratio of $5\times10^3$ cells/well, and cultured in 2S-containing DMEM added with the peptide (a) or (c) at various concentrations and adjusted by addition of 10 mM sodium β-glycerophosphate. Three weeks after the cells reached a confluent state, the cells were washed with PBS, fixed with neutrally buffered formalin and stained with alizarin red S (Wako Pure Chemical Industries).

As a result, when the peptide (a) or (c) was added, the calcification ability of the PDL cells significantly increased. Therefore, it was demonstrated that the peptides (a) and (c) had a cell differentiation promoting effect.

Further, the peptide (a), BMP2 and TGFβ were similarly examined by using the MC3T3 cells. As a result of the assessment two weeks after a confluent state was attained, the peptide (a) exhibited a significant cell differentiation promoting effect not only on the PDL cells but also on the MC3T3 cells. Further, this effect was comparable to or higher than that of BMP2. These results also demonstrated that the peptide (a) had an extremely high cell differentiation promoting effect.

Example 3

Pharmacological Study 1 Using Animals

The following experiment was performed in order to examine action of the peptide of the present invention on a periodontal disease model.

(i) Preparation of Periodontal Disease Model 8-week old Wistar rats were systemically anesthetized with an ethyl carbamate solution in a volume of 0.5 ml per 100 g of body weight, and then the mesial gingiva of each first molar on the upper jaw was vertically incised. The gingival periosteal flap was reflected to expose the mesial alveolar bone of the first molar. Then, a defect having a length of about 2 mm and a buccolingual diameter of about 1 mm was formed from the alveolar bone crest of the same site towards the root apex side by using a fissure bur under pouring saline to expose the mesial root face of the first molar on the upper jaw. The root cementum and surface of dentin was removed together with the periodontal ligament attached to the exposed root face so as to make a shallow cavity.

(ii) Test Method

At the aforementioned defect, a sample prepared with 1% PBS solution of sodium hyaluronate (weight average molecular weight: 900,000) was applied on the exposed root face, and the gingival periosteal flap was repositioned and sutured. By using a group of the animals applied with 1% PBS solution of sodium hyaluronate containing the peptide (a) (concentration of the peptide (a): 0.3 mg/ml) as the peptide group, a group of the animals applied with 1% PBS solution of sodium hyaluronate alone as the hyaluronic acid group, and a group of the animals applied with no substance before suture of the gingival periosteal flap for restoration as the control group, healing conditions were compared one month after the operation.

(Method for Preparing Histological Specimens)

The animals were euthanized with chloroform, and each experimental site was excised. The excised upper jaw bone was fixed by immersion in neutrally buffered formalin for 1 day and then decalcified over 2 days by using a rapid decalcifying solution (K-CX). The specimen was embedded in paraffin in a conventional manner, then a mesiodistal section having a thickness of 4.5 mm and parallel to the longitudinal axis of the tooth root was prepared at the experiment site and stained with hematoxylin/eosin. Adhesion condition of periodontal tissue to the exposed surface of the tooth root at the defective site and the position of the apex of the alveolar bone were evaluated light microscopically.

(iii) Results (Findings)

Whilst down-growth of the epithelium was observed in both of the control group and the hyaluronic acid group, it was observed to a less extent in the peptide group. Further, depositions of cementum and cementum with insertion of Sharpey's fibers were hardly observed in both of the control group and the hyaluronic acid group, and separation was often observed between the gingiva and the tooth root. On the other hand, no such separation was observed in the peptide group, and on the surface of the exposed root, deposition of cementum with Sharpey's fibers, that is, new connective tissue attachment formation, was observed. Further, the bone regeneration was more active than in the other two groups, and high bone regeneration ability was observed.

Example 4

Pharmacological Study 2 Using Animals

The following experiment was performed in order to examine action of the peptide of the present invention on a bone loss model.

(i) Preparation of Bone Loss Model

Male Wistar rats (8-week old) were systemically anesthetized with an ethyl carbamate solution in a volume of 0.5 ml per 100 g of body weight, then the skin of the right and left hind leg tibiae and the periostium of tibiae were incised, and the periostium were reflected to expose the tibiae. Then, a hole having a diameter of 2 mm was perforated in the cortical bone at the same site by using a round bur under pouring physiological saline to form a defect reaching the medullary cavity (diameter: 2 mm, depth: 3 mm).

(ii) Test Method

The bone loss site was filled with the peptide (a) (concentration: 0.3 mg/ml or 3 mg/ml) dissolved in a sodium hyaluronate preparation (trade name: ARTZ (registered trade mark), weight average molecular weight of sodium hyaluronate: about 900,000, concentration of sodium hyaluronate: 1%), and the periost and the skin were repositioned and sutured. Healing conditions of the animals 3 weeks after the operation in a group of animals filled with the peptide (peptide group), a group of animals applied with 1% PBS solution of sodium hyaluronate as a vehicle alone (HA group) and a group of animals applied with no substance before the suture of the skin periosteal flap (control group) were examined by using X-ray.

(iii) Results

In comparison of soft X-ray images for the groups, whereas the remaining bone loss was relatively clearly observed in the control group and the HA group, it was confirmed in the peptide group (concentration: 0.3 mg/ml or 3 mg/ml) that bone had been regenerated to such an extent that bone loss could hardly be recognized. These results demonstrated that the peptide of the present invention significantly promoted bone regeneration at the bone loss site.

(iv) Other Effects of the Peptide of the Present Invention

In a similar manner, experiments were performed with collagen gel (trade name: Koken Atelocollagen Implant, Koken) and the peptides (a) and (b) (concentration: 3 mg/ml). As a result, whereas the remaining bone loss was relatively clearly observed in the control group and the collagen gel group, it was confirmed that bone had been regenerated to such an extent that bone loss could hardly be recognized not only when the peptide (a) was used but also when the peptide (b) was used. These results demonstrated that the peptide of the present invention significantly promoted bone regeneration at the bone loss site.

Example 5

Preparation Example 1

Preparation examples of the agent of the present invention will be described below. However, these are mere examples, and the dosage form of the agent of the present invention is not limited to these.

(1) Ointment

| Peptide (a) produced above | 10 mg |
| --- | --- |
| Sorbitan monostearate | 7 mg |
| Polyoxyethylene sorbitan monostearate | 7 mg |
| Isopropyl palmitate | 37 mg |
| Vaseline | 37 mg |
| Liquid paraffin | 37 mg |
| Cetanol | 50 mg |
| Glycerol | 70 mg |
| Magnesium stearate | 2 mg |

Purified water was added to the above ingredients to obtain 1 g of cream.

(2) Tablet

| Peptide (b) produced above | 100 mg |
| --- | --- |
| Lactose | 670 mg |
| Potato starch | 150 mg |
| Crystalline cellulose | 60 mg |
| Light anhydrous silicic acid | 50 mg |

The above ingredients were mixed, added with a solution of 30 mg of hydroxypropylcellulose dissolved in methanol (10% by weight of hydroxypropylcellulose), kneaded and then pelletized. The pellets were extruded through a screen with apertures of 0.8 mm in diameter, formed into granules, dried, then added with 15 mg of magnesium stearate and compressed as 200-mg portions to obtain tablets.

(3) Capsule

| Peptide (b) produced above | 100 mg |
| --- | --- |
| Lactose | 80 mg |

A capsule was produced by uniformly mixing the above ingredients and filling the mixture in a hard capsule.

(4) Injection

| Peptide (a) produced above | 30 mg |
| --- | --- |

The above ingredient was dissolved in 2 mL of 5% aqueous mannitol and subjected to aseptic filtration, filled in an ampoule and then sealed.

(5) Injection to be Dissolved Upon Use

| (A) Peptide (b) produced above (lyophilized) (filled in an ampoule) | 30 mg |
| --- | --- |
| (B) PBS subjected to aseptic filtration (filled in an ampoule) | 2 mL |

An injection to be dissolved upon use was produced with (A) and (B) mentioned above as 1 set. The injection can be used by dissolving (A) in (B) when used.

Example 6

Production Example 2

Production examples of the composition of the present invention will be described below. However, these are mere examples, and composition, form and so forth of the composition of the present invention are not limited to these.

(1) Composition in Liquid State

| Peptide (a) produced above | 3 mg |
| --- | --- |
| 1% PBS solution of sodium hyaluronate (weight average molecular weight: 900,000) | 10 ml |

The composition of the present invention in a liquid state was produced by mixing the above ingredients.

(2) Composition in Liquid State

| Peptide (a) produced in the above | 3 mg |
| --- | --- |
| 0.1% PBS solution of sodium hyaluronate (weight average molecular weight: 2,200,000) | 10 ml |

The composition of the present invention in a liquid state was produced by mixing the above ingredients.

(3) Composition in Dry State

| Peptide (b) produced above | 30 mg |
| --- | --- |
| 1% PBS solution of sodium hyaluronate (weight average molecular weight: 900,000) | 10 ml |

The composition of the present invention in a dry state was produced by mixing the above ingredients and lyophilizing the mixture.

Sheathlin having the amino acid sequence of the peptide of the present invention has already been used as an ingredient of therapeutic agents for periodontal diseases. Further, during addition (or administration) of the peptides of the present invention in the aforementioned pharmacological studies, conditions of the cells and animals were examined every day, and no particular change was observed. On the basis of these findings, safety of the peptide of the present invention and the agent of the present invention can be sufficiently estimated. Further, because hyaluronic acid or a pharmaceutically acceptable salt thereof has already been used as an active ingredient of pharmaceuticals, safety of the composition of the present invention can also be sufficiently estimated.

INDUSTRIAL APPLICABILITY

Because the peptide of the present invention is a partial peptide of the sheathlin molecule and exhibits markedly higher cell growth activity and cell differentiation promoting activity compared with sheathlin, it is extremely useful as an active ingredient of the agent of the present invention, in particular, agent for promoting cell growth, agent for promoting cell differentiation or agent for promoting formation or regeneration of bone, cartilage or periodontal tissue. Further, the peptide of the present invention can be used as a material for regenerative medicine or the like, and it is also extremely useful from this point of view.

Further, because the peptide of the present invention exhibits a very high biological activity as described above, the amount of the active ingredient in the agent of the present invention containing the peptide of the present invention as an active ingredient can be reduced. Therefore, a safe and less expensive agent of the present invention or the like can be provided.

The agent of the present invention can be used for various purposes such as promotion of cell growth, promotion of cell differentiation and promotion of formation or regeneration of bone, cartilage or periodontal tissue, and therefore it is extremely useful.

With the composition of the present invention, the effects that the peptide of the present invention is retained at an objective site, the peptide of the present invention is gradually released at the objective site, and so forth are obtained by the physicochemical properties of hyaluronic acid or a pharmaceutically acceptable salt thereof. Therefore, the composition of the present invention is extremely useful. Further, the composition of the present invention would be extremely useful because it is likely that even more advantageous biological effects may be exhibited by addition of the biological properties of hyaluronic acid or a pharmaceutically acceptable salt to those of the peptide of the present invention.

What is claimed is:

1. A peptide consisting of the following amino acid sequence (SEQ ID NO: 13):

Asn Lys X26 X27 X28 Pro X28 X29 X30 X31 X32 Ala Trp X31 Phe wherein X26 represents Ala or Val, X27 represents Gln or His, X28 represents Gln or Glu, X29 represents Ile, Met or Val, X30 indicates absence of amino acid residue or represents Lys or Met, X31 represents Arg or His, and X32 represents Asp or Asn.

2. The peptide according to claim 1, which consists of the following amino acid sequence (SEQ ID NO: 14):

Asn Lys Ala Gln X33 Pro X33 X34 X35 X36 Asp Ala Trp X36 Phe wherein X33 represents Gln or Glu, X34 represents Ile or Met, X35 represents Lys or Met, and X36 represents Arg or His.

3. The peptide according to claim 1, which consists of any of the following amino acid sequences (H) to (K):

(H) Asn Lys Ala Gln Gln Pro Gln Ile Lys Arg Asp Ala Trp Arg Phe (SEQ ID NO: 10)

(I) Asn Lys Ala Gln Glu Pro Glu Met Met His Asp Ala Trp His Phe (SEQ ID NO: 15)

(J) Asn Lys Ala Gln Gln Pro Gln Ile Lys His Asp Ala Trp His Phe (SEQ ID NO: 16)

(K) Asn Lys Val His Gln Pro Gln Val His Asn Ala Trp Arg Phe. (SEQ ID NO: 17)

4. A composition comprising the peptide according to any one of claims 1 to 3 and hyaluronic acid or a pharmaceutically acceptable salt thereof.

5. The composition according to claim 4, which is a pharmaceutical.

6. The composition according to claim 4, which is a composition for promoting cell growth.

7. The composition according to claim 6, wherein the cell is an osteoblast, chondroblast, cementoblast, bone marrow-derived mesenchymal stem cell or periodontal ligament-derived cell.

8. The composition according to claim 4, which is a composition for promoting cell differentiation.

9. The composition according to claim 8, wherein the cell is an osteoblast, chondroblast, cementoblast, bone marrow-derived mesenchymal stem cell or periodontal ligament-derived cell.

10. The composition according to claim 4, which is a composition for promoting bone or cartilage formation or regeneration.

11. The composition according to claim 4, which is a composition for promoting periodontal tissue formation or regeneration.

* * * * *

UNITED STATES PATENT AND TRADEMARK OFFICE
CERTIFICATE OF CORRECTION

| | | |
|---|---|---|
| PATENT NO. | : 7,678,884 B2 | Page 1 of 1 |
| APPLICATION NO. | : 12/052578 | |
| DATED | : March 16, 2010 | |
| INVENTOR(S) | : Takata et al. | |

It is certified that error appears in the above-identified patent and that said Letters Patent is hereby corrected as shown below:

On the Title page, item [56]: Page 1, Column 2, Line 16, "*Chemisty*, Vol. 271," should be changed to --*Chemistry*, Vol. 271,--

Column 1, Line 39, "immunolocalozation of porcine" should be changed to
    --immunolocalization of porcine--

Column 7, Line 34, "Kato T. Aoyagi H," should be changed to --Kato T, Aoyagi H,--

Column 7, Line 48, "which Nα-and" should be changed to --which Nα- and--

Column 7, Line 52, "Nα-and side-chain" should be changed to --Nα- and side-chain--

Columns 17-18, Line 4, "Aia Ser Leu" should be changed to --Ala Ser Leu--

Column 22, Line 1, "with the peptide (b)" should be changed to --with the peptide (b).--

Column 37, Line 44, "Ala Gin X33" should be changed to --Ala Gln X33--

Column 37, Line 46, "represents Gin or Glu," should be changed to --represents Gln or Glu,--

Signed and Sealed this

Twenty-eighth Day of September, 2010

David J. Kappos
*Director of the United States Patent and Trademark Office*

SEQUENCE LISTING

```
<160> NUMBER OF SEQ ID NOS: 25

<210> SEQ ID NO 1
<211> LENGTH: 21
<212> TYPE: PRT
<213> ORGANISM: Artificial
<220> FEATURE:
<223> OTHER INFORMATION: A partial peptide of sheathlin wherein Xaa at
      position 1 = Val or Gln, Xaa at position 3 = Ala, Phe or Gly, Xaa
      at position 4 = Phe or Leu, Xaa at position 5 = Pro or Lys, Xaa at
      position 6 = Arg, Gln or Pro, Xaa at position 7 = Gln, Arg or Phe,
      Xaa at position 8 = Pro, Ser or Leu, Xaa at position 9 = none, Gly
      or Gln, Xaa at position 10 = none, Ala, Gly or Pro, Xaa at
      position 11 = none, Gln or Thr, Xaa at position 12 = none, Gly or
      Ala, Xaa at position 13 = none, Met or Ala, Xaa at position 14 =
      Gly, Ala or Thr, Xaa at position 15 = Thr, Ile, Pro or Gly, Xaa at
      position 16 = Pro or Val, Xaa at position 17 = Gly or Gln, Xaa at
      position 18 = Val, Met or Gly, Xaa at position 19 = Ala or Thr,
      Xaa at position 20 = Ser or Pro, and Xaa at position 21 = Leu or
      Gln.

<400> SEQUENCE: 1

Xaa Pro Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 2
<211> LENGTH: 16
<212> TYPE: PRT
<213> ORGANISM: Artificial
<220> FEATURE:
<223> OTHER INFORMATION: A partial peptide of sheathlin wherein Xaa at
      position 3 = Ala or Phe, Xaa at position 6 = Arg or Gln, Xaa at
      position 8 = Pro or Ser, Xaa at position 10 = Thr or Ile, and Xaa
      at position 13 = Val, Met or Gly.

<400> SEQUENCE: 2

Val Pro Xaa Phe Pro Xaa Gln Xaa Gly Xaa Pro Gly Xaa Ala Ser Leu
1               5                   10                  15

<210> SEQ ID NO 3
```

```
<211> LENGTH: 16
<212> TYPE: PRT
<213> ORGANISM: Artificial
<220> FEATURE:
<223> OTHER INFORMATION: A partial peptide of sheathlin.

<400> SEQUENCE: 3

Val Pro Ala Phe Pro Arg Gln Pro Gly Thr Pro Gly Val Ala Ser Leu
1               5                   10                  15

<210> SEQ ID NO 4
<211> LENGTH: 16
<212> TYPE: PRT
<213> ORGANISM: Artificial
<220> FEATURE:
<223> OTHER INFORMATION: A partial peptide of sheathlin.

<400> SEQUENCE: 4

Val Pro Phe Phe Pro Gln Gln Ser Gly Thr Pro Gly Met Ala Ser Leu
1               5                   10                  15

<210> SEQ ID NO 5
<211> LENGTH: 16
<212> TYPE: PRT
<213> ORGANISM: Artificial
<220> FEATURE:
<223> OTHER INFORMATION: A partial peptide of sheathlin.

<400> SEQUENCE: 5

Val Pro Ala Phe Pro Gln Gln Pro Gly Ile Pro Gly Met Ala Ser Leu
1               5                   10                  15

<210> SEQ ID NO 6
<211> LENGTH: 21
<212> TYPE: PRT
<213> ORGANISM: Artificial
<220> FEATURE:
<223> OTHER INFORMATION: A partial peptide of sheathlin.

<400> SEQUENCE: 6

Val Pro Ala Phe Pro Gln Gln Pro Gly Ala Gln Gly Met Ala Pro Pro
1               5                   10                  15

Gly Met Ala Ser Leu
            20

<210> SEQ ID NO 7
<211> LENGTH: 21
<212> TYPE: PRT
<213> ORGANISM: Artificial
<220> FEATURE:
<223> OTHER INFORMATION: A partial peptide of sheathlin.

<400> SEQUENCE: 7

Val Pro Ala Phe Pro Gln Arg Pro Gly Gly Gln Gly Met Ala Pro Pro
1               5                   10                  15

Gly Met Ala Ser Leu
            20

<210> SEQ ID NO 8
<211> LENGTH: 21
<212> TYPE: PRT
<213> ORGANISM: Artificial
<220> FEATURE:
<223> OTHER INFORMATION: A partial peptide of sheathlin.
```

-continued

```
<400> SEQUENCE: 8

Gln Pro Gly Leu Lys Pro Phe Leu Gln Pro Thr Ala Ala Thr Gly Val
1               5                   10                  15

Gln Val Thr Pro Gln
            20

<210> SEQ ID NO 9
<211> LENGTH: 16
<212> TYPE: PRT
<213> ORGANISM: Artificial
<220> FEATURE:
<223> OTHER INFORMATION: A partial peptide of sheathlin.

<400> SEQUENCE: 9

Val Pro Phe Phe Pro Gln Gln Ser Gly Thr Pro Gly Gly Ala Ser Leu
1               5                   10                  15

<210> SEQ ID NO 10
<211> LENGTH: 15
<212> TYPE: PRT
<213> ORGANISM: Artificial
<220> FEATURE:
<223> OTHER INFORMATION: A partial peptide of sheathlin.

<400> SEQUENCE: 10

Asn Lys Ala Gln Gln Pro Gln Ile Lys Arg Asp Ala Trp Arg Phe
1               5                   10                  15

<210> SEQ ID NO 11
<211> LENGTH: 10
<212> TYPE: PRT
<213> ORGANISM: Artificial
<220> FEATURE:
<223> OTHER INFORMATION: A partial peptide of sheathlin.

<400> SEQUENCE: 11

Glu His Glu Thr Gln Gln Tyr Glu Tyr Ser
1               5                   10

<210> SEQ ID NO 12
<211> LENGTH: 13
<212> TYPE: PRT
<213> ORGANISM: Artificial
<220> FEATURE:
<223> OTHER INFORMATION: A partial peptide of sheathlin.

<400> SEQUENCE: 12

Ala Arg Gly Pro Ala Gly Arg Ser Arg Gly Pro Pro Gly
1               5                   10

<210> SEQ ID NO 13
<211> LENGTH: 15
<212> TYPE: PRT
<213> ORGANISM: Artificial
<220> FEATURE:
<223> OTHER INFORMATION: A partial peptide of sheathlin wherein Xaa at
      position 3 = Ala or Val, Xaa at position 4 = Gln or His, Xaa at
      position 5 = Gln or Glu, Xaa at position 7 = Gln or Glu, Xaa at
      position 8 = Ile, Met or Val, Xaa at position 9 = none, Lys or
      Met, Xaa at position 10 = Arg or His, Xaa at position 11 = Asp or
      Asn, and Xaa at position 14 = Arg or His.
```

-continued

```
<400> SEQUENCE: 13

Asn Lys Xaa Xaa Xaa Pro Xaa Xaa Xaa Xaa Xaa Ala Trp Xaa Phe
1               5                   10                  15

<210> SEQ ID NO 14
<211> LENGTH: 15
<212> TYPE: PRT
<213> ORGANISM: Artificial
<220> FEATURE:
<223> OTHER INFORMATION: A partial peptide of sheathlin wherein Xaa at
      position 5 = Gln or Glu, Xaa at position 7 = Gln or Glu, Xaa at
      position 8 = Ile or Met, Xaa at position 9 = Lys or Met, Xaa at
      position 10 = Arg or His, and Xaa at position 14 = Arg or His.

<400> SEQUENCE: 14

Asn Lys Ala Gln Xaa Pro Xaa Xaa Xaa Xaa Asp Ala Trp Xaa Phe
1               5                   10                  15

<210> SEQ ID NO 15
<211> LENGTH: 15
<212> TYPE: PRT
<213> ORGANISM: Artificial
<220> FEATURE:
<223> OTHER INFORMATION: A partial peptide of sheathlin.

<400> SEQUENCE: 15

Asn Lys Ala Gln Glu Pro Glu Met Met His Asp Ala Trp His Phe
1               5                   10                  15

<210> SEQ ID NO 16
<211> LENGTH: 15
<212> TYPE: PRT
<213> ORGANISM: Artificial
<220> FEATURE:
<223> OTHER INFORMATION: A partial peptide of sheathlin.

<400> SEQUENCE: 16

Asn Lys Ala Gln Gln Pro Gln Ile Lys His Asp Ala Trp His Phe
1               5                   10                  15

<210> SEQ ID NO 17
<211> LENGTH: 14
<212> TYPE: PRT
<213> ORGANISM: Artificial
<220> FEATURE:
<223> OTHER INFORMATION: A partial peptide of sheathlin.

<400> SEQUENCE: 17

Asn Lys Val His Gln Pro Gln Val His Asn Ala Trp Arg Phe
1               5                   10

<210> SEQ ID NO 18
<211> LENGTH: 12
<212> TYPE: PRT
<213> ORGANISM: Artificial
<220> FEATURE:
<223> OTHER INFORMATION: A partial peptide of sheathlin.

<400> SEQUENCE: 18

Val Pro Phe Phe Pro Gln Gln Ser Gly Thr Pro Gly
1               5                   10
```

```
<210> SEQ ID NO 19
<211> LENGTH: 8
<212> TYPE: PRT
<213> ORGANISM: Artificial
<220> FEATURE:
<223> OTHER INFORMATION: A partial peptide of sheathlin.

<400> SEQUENCE: 19

Val Pro Phe Phe Pro Gln Gln Ser
1               5

<210> SEQ ID NO 20
<211> LENGTH: 8
<212> TYPE: PRT
<213> ORGANISM: Artificial
<220> FEATURE:
<223> OTHER INFORMATION: A partial peptide of sheathlin.

<400> SEQUENCE: 20

Pro Gln Gln Ser Gly Thr Pro Gly
1               5

<210> SEQ ID NO 21
<211> LENGTH: 9
<212> TYPE: PRT
<213> ORGANISM: Artificial
<220> FEATURE:
<223> OTHER INFORMATION: A partial peptide of sheathlin.

<400> SEQUENCE: 21

Ser Gly Thr Pro Gly Met Ala Ser Leu
1               5

<210> SEQ ID NO 22
<211> LENGTH: 12
<212> TYPE: PRT
<213> ORGANISM: Artificial
<220> FEATURE:
<223> OTHER INFORMATION: A partial peptide of sheathlin.

<400> SEQUENCE: 22

Pro Gln Gln Ser Gly Thr Pro Gly Met Ala Ser Leu
1               5                   10

<210> SEQ ID NO 23
<211> LENGTH: 20
<212> TYPE: PRT
<213> ORGANISM: Artificial
<220> FEATURE:
<223> OTHER INFORMATION: A partial peptide of sheathlin.

<400> SEQUENCE: 23

Met Ser Phe Ala Val Pro Phe Phe Pro Gln Gln Ser Gly Thr Pro Gly
1               5                   10                  15

Met Ala Ser Leu
            20

<210> SEQ ID NO 24
<211> LENGTH: 20
<212> TYPE: PRT
<213> ORGANISM: Artificial
<220> FEATURE:
<223> OTHER INFORMATION: A partial peptide of sheathlin.
```

-continued

```
<400> SEQUENCE: 24

Val Pro Phe Phe Pro Gln Gln Ser Gly Thr Pro Gly Met Ala Ser Leu
1               5                   10                  15

Ser Leu Glu Thr
            20

<210> SEQ ID NO 25
<211> LENGTH: 20
<212> TYPE: PRT
<213> ORGANISM: Artificial
<220> FEATURE:
<223> OTHER INFORMATION: A partial peptide of sheathlin.

<400> SEQUENCE: 25

Phe Ala Val Pro Phe Phe Pro Gln Gln Ser Gly Thr Pro Gly Met Ala
1               5                   10                  15

Ser Leu Ser Leu
            20
```